(12) United States Patent
Sharonov

(10) Patent No.: US 9,439,712 B2
(45) Date of Patent: Sep. 13, 2016

(54) HEAT-DISTRIBUTION INDICATORS, THERMAL ZONE INDICATORS, ELECTROSURGICAL SYSTEMS INCLUDING SAME AND METHODS OF DIRECTING ENERGY TO TISSUE USING SAME

(71) Applicant: COVIDIEN LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 587 days.

(21) Appl. No.: 13/920,411

(22) Filed: Jun. 18, 2013

(65) Prior Publication Data

US 2014/0018677 A1    Jan. 16, 2014

Related U.S. Application Data

(60) Provisional application No. 61/670,965, filed on Jul. 12, 2012.

(51) Int. Cl.
*A61B 8/12* (2006.01)
*A61B 18/12* (2006.01)
(Continued)

(52) U.S. Cl.
CPC .............. *A61B 18/12* (2013.01); *A61B 5/015* (2013.01); *A61B 5/053* (2013.01); *A61B 5/4836* (2013.01); *A61B 8/08* (2013.01); *A61B 8/13* (2013.01); *A61B 8/5223* (2013.01); *A61B 18/1477* (2013.01); *A61B 18/1815* (2013.01); *A61N 1/08* (2013.01); *A61B 2018/00023* (2013.01); *A61B 2018/0072* (2013.01); *A61B 2018/00577* (2013.01); *A61B 2018/00642* (2013.01); *A61B 2018/00702* (2013.01); *A61B 2018/00708* (2013.01); *A61B 2018/00714* (2013.01); *A61B 2018/00755* (2013.01);
(Continued)

(58) Field of Classification Search
None
See application file for complete search history.

(56) References Cited

U.S. PATENT DOCUMENTS

D223,367 S    4/1972 Kountz
D263,020 S    2/1982 Rau, III
(Continued)

FOREIGN PATENT DOCUMENTS

CN    1103807    6/1995
DE    390937    3/1924
(Continued)

OTHER PUBLICATIONS

Partial European Search Report dated Oct. 1, 2013 for EP 13 17 5303.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
(Continued)

*Primary Examiner* — Long V Le
*Assistant Examiner* — Bradley Impink

(57) ABSTRACT

An electrosurgical system includes an electrosurgical power generating source, an energy applicator operably associated with the electrosurgical power generating source, a heat-distribution indicator adapted to change echogenic properties in response to heat generated by energy delivered by the energy applicator, and a processor unit configured to generate at least one electrical signal for controlling at least one operating parameter associated with the electrosurgical power generating source. The system also includes an imaging system capable of acquiring image data. The imaging system is communicatively-coupled to the processor unit. The processor unit is adapted to determine an ablation rate at least in part based on analysis of one or more images acquired by the imaging system.

15 Claims, 12 Drawing Sheets

(51) Int. Cl.

| | |
|---|---|
| *A61B 8/13* | (2006.01) |
| *A61B 5/01* | (2006.01) |
| *A61B 5/053* | (2006.01) |
| *A61B 5/00* | (2006.01) |
| *A61B 8/08* | (2006.01) |
| *A61N 1/08* | (2006.01) |
| *A61B 18/18* | (2006.01) |
| *A61B 18/14* | (2006.01) |
| *A61B 18/00* | (2006.01) |

(52) U.S. Cl.
CPC ........... *A61B 2018/00761* (2013.01); *A61B 2018/00767* (2013.01); *A61B 2018/00791* (2013.01); *A61B 2018/00904* (2013.01); *A61B 2018/00994* (2013.01); *A61B 2018/143* (2013.01); *A61B 2018/1838* (2013.01); *A61B 2018/1853* (2013.01); *A61B 2018/1869* (2013.01)

(56) References Cited

U.S. PATENT DOCUMENTS

| | | |
|---|---|---|
| D266,842 S | 11/1982 | Villers et al. |
| D278,306 S | 4/1985 | McIntosh |
| 4,669,475 A | 6/1987 | Turner |
| D295,893 S | 5/1988 | Sharkany et al. |
| D295,894 S | 5/1988 | Sharkany et al. |
| 4,869,259 A | 9/1989 | Elkins |
| 4,971,068 A | 11/1990 | Sahi |
| 5,220,927 A | 6/1993 | Astrahan et al. |
| 5,370,675 A | 12/1994 | Edwards et al. |
| D354,218 S | 1/1995 | Van de Peer |
| 5,560,712 A | 10/1996 | Kleinerman |
| 6,002,968 A | 12/1999 | Edwards |
| D424,693 S | 5/2000 | Pruter |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| 6,478,793 B1 | 11/2002 | Cosman et al. |
| 6,530,922 B2 | 3/2003 | Cosman et al. |
| 6,575,969 B1 * | 6/2003 | Rittman, III ........ A61B 18/1482 128/898 |
| D487,039 S | 2/2004 | Webster et al. |
| D496,997 S | 10/2004 | Dycus et al. |
| D499,181 S | 11/2004 | Dycus et al. |
| 6,984,993 B2 | 1/2006 | Ariav |
| 7,065,394 B2 | 6/2006 | Hobot et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,220,259 B2 | 5/2007 | Harrington et al. |
| D564,662 S | 3/2008 | Moses et al. |
| 7,387,626 B2 | 6/2008 | Edwards et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| D681,810 S | 5/2013 | Decarlo |
| 2002/0026188 A1 * | 2/2002 | Balbierz ............ A61B 18/1206 606/41 |
| 2002/0111617 A1 * | 8/2002 | Cosman ............ A61B 18/1485 606/41 |
| 2003/0083654 A1 | 5/2003 | Chin et al. |
| 2004/0186469 A1 | 9/2004 | Woloszko et al. |
| 2005/0203507 A1 | 9/2005 | Truckai et al. |
| 2006/0100693 A1 | 5/2006 | Walak et al. |
| 2006/0224156 A1 | 10/2006 | Arts et al. |
| 2007/0050000 A1 | 3/2007 | Esch et al. |
| 2008/0125775 A1 | 5/2008 | Morris |
| 2008/0183165 A1 | 7/2008 | Buysse et al. |
| 2008/0319525 A1 | 12/2008 | Tieu et al. |
| 2011/0054459 A1 | 3/2011 | Peterson |
| 2011/0118714 A1 | 5/2011 | Deladi et al. |
| 2011/0152994 A1 | 6/2011 | Hendriksen et al. |
| 2011/0301590 A1 | 12/2011 | Podhajsky et al. |
| 2012/0161786 A1 | 6/2012 | Brannan |
| 2012/0165806 A1 | 6/2012 | Brannan |
| 2013/0041251 A1 * | 2/2013 | Bailey ................ A61B 5/076 600/424 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |

(56) References Cited

FOREIGN PATENT DOCUMENTS

| | | |
|---|---|---|
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| KR | 20070093068 | 9/2007 |
| KR | 20100014406 | 2/2010 |
| KR | 20120055063 | 5/2012 |
| SU | 166452 | 11/1964 |
| SU | 401367 | 11/1974 |
| SU | 727201 | 4/1980 |
| WO | 8702769 A1 | 5/1987 |
| WO | WO00/36985 | 6/2000 |
| WO | WO2008/144341 | 11/2008 |
| WO | WO2010/035831 | 4/2010 |
| WO | 2010102117 A1 | 9/2010 |
| WO | WO 2011/084957 A1 | 7/2011 |
| WO | WO 2011/088393 A2 | 7/2011 |
| WO | 2012071388 A2 | 5/2012 |

OTHER PUBLICATIONS

U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.

(56) References Cited

OTHER PUBLICATIONS

E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite •Element Codes to Model Electrical Heating and Non •Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817•825.

Urologix, Inc.-Medical Professionals: Targis™ Technology, "Overcoming the Challenge" located at: <http://www.urologix.com-!medicaUtechnology.html > Nov. 18, 1999; 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation-'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

European Search Report, Application No. EP 13 18 6382 dated Feb. 27, 2014.

\* cited by examiner

HEAT-DISTRIBUTION INDICATORS, THERMAL ZONE INDICATORS, ELECTROSURGICAL SYSTEMS INCLUDING SAME AND METHODS OF DIRECTING ENERGY TO TISSUE USING SAME

CROSS REFERENCE TO RELATED APPLICATION

The present application claims the benefit of and priority to U.S. Provisional Application Ser. No. 61/670,965, filed on Jul. 12, 2012, the entire contents of which are incorporated herein by reference.

BACKGROUND

1. Technical Field

The present disclosure relates to systems, devices and methods for performing a medical procedure. More particularly, the present disclosure relates to heat-distribution indicators and thermal zone indicators suitable for use during thermal ablation, electrosurgical systems including the same, and methods of directing energy to tissue using the same.

2. Discussion of Related Art

Electrosurgery is the application of electricity and/or electromagnetic energy to cut, dissect, ablate, coagulate, cauterize, seal or otherwise treat biological tissue during a surgical procedure. When electrical energy and/or electromagnetic energy is introduced to tissue, the energy-tissue interaction produces excitation of molecules, creating molecular motion that results in the generation of heat. Electrosurgery is typically performed using a handpiece including a surgical instrument (e.g., end effector, ablation probe, or electrode) adapted to transmit energy to a tissue site during electrosurgical procedures, an electrosurgical generator operable to output energy, and a cable assembly operatively connecting the surgical instrument to the generator.

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue. The application of ultrasound imaging is one of the cost-effective methods often used for tumor localization and ablation device placement.

There are a number of different types of apparatus that can be used to perform ablation procedures. Typically, apparatus for use in ablation procedures include a power generating source, e.g., a microwave or radio frequency (RF) electrosurgical generator, that functions as an energy source, and a surgical instrument (e.g., microwave ablation probe having an antenna assembly) for directing the energy to the target tissue. The generator and surgical instrument are typically operatively coupled by a cable assembly having a plurality of conductors for transmitting energy from the generator to the instrument, and for communicating control, feedback and identification signals between the instrument and the generator.

Using electrosurgical instruments to ablate, seal, cauterize, coagulate, and/or desiccate tissue may result in some degree of thermal injury to surrounding tissue. For example, electrosurgical desiccation may result in undesirable tissue damage due to thermal effects, wherein otherwise healthy tissue surrounding the tissue to which the electrosurgical energy is being applied is thermally damaged by an effect known in the art as "thermal spread". During the occurrence of thermal spread, excess heat from the operative site can be directly conducted to the adjacent tissue and/or the release of steam from the tissue being treated at the operative site can result in damage to the surrounding tissue. The duration of the activation of the generator is directly related to the heat produced in the tissue. The greater the heat produced, the more the potential for thermal spread to adjacent tissues.

Currently available systems and methods for controlling an electrosurgical generator during electrosurgery may include a clinician monitoring and adjusting, as necessary, the amount of energy delivered to a tissue site through current, voltage, impedance, and/or power measurements such that an appropriate tissue effect can be achieved at the tissue site with minimal collateral damage resulting to adjacent tissue. These systems and/or methods typically require a clinician to translate the desired tissue effect to a power setting on an electrosurgical generator and, if necessary, adjust the power setting to compensate for tissue transformations (e.g., desiccation of tissue) associated with the electrosurgical procedure such that a desired tissue effect may be achieved.

As can be appreciated, limiting the possibility of thermal spread or the like during an electrosurgical procedure reduces the likelihood of unintentional and/or undesirable collateral damage to surrounding tissue structures which may be adjacent to an intended treatment site. Controlling and/or monitoring the depth of thermal spread during an electrosurgical procedure may aid a clinician in assessing tissue modification and/or transformation during the electrosurgical procedure.

Medical imaging has become a significant component in the clinical setting and in basic physiology and biology research, e.g., due to enhanced spatial resolution, accuracy and contrast mechanisms that have been made widely available. Medical imaging now incorporates a wide variety of modalities that noninvasively capture the structure and function of the human body. Such images are acquired and used in many different ways including medical images for diagnosis, staging and therapeutic management of malignant disease.

Because of their anatomic detail, computed tomography (CT) and magnetic resonance imaging (MRI) are suitable for, among other things, evaluating the proximity of tumors to local structures. CT and MRI scans produce two-dimensional (2-D) axial images, or slices, of the body that may be viewed sequentially by radiologists who visualize or extrapolate from these views actual three-dimensional (3-D) anatomy.

Measurements and quantitative analysis for parameters such as area, perimeter, volume and length may be obtained when object boundaries are defined. A boundary in an image is a contour that represents the change from one object or surface to another. Image segmentation involves finding salient regions and their boundaries. A number of image segmentation methods have been developed using fully automatic or semi-automatic approaches for medical imaging and other applications. Medical image segmentation refers to the delineation of anatomical structures and other regions of interest in medical images for assisting clinicians in evaluating medical imagery or in recognizing abnormal findings in a medical image. Structures of interest may include organs or parts thereof, such as cardiac ventricles or kidneys, abnormalities such as tumors and cysts, as well as other structures such as bones and vessels.

Medical image processing, analysis and visualization play an increasingly significant role in disease diagnosis and monitoring as well as, among other things, surgical planning and monitoring of therapeutic procedures. Unfortunately, tissue heating and thermal damage does not create adequate contrast in ultrasound images to allow determination of the size of an ablated zone and assessment of the margins of ablated tissue.

SUMMARY

A continuing need exists for systems, devices and methods for controlling and/or monitoring real-time tissue effects to improve patient safety, reduce risk, and/or improve patient outcomes. There is a need for intraoperative techniques for ablation margin assessment and feedback control.

According to an aspect of the present disclosure, a device for assessing the progress of a heating process is provided. The device includes an elongated member and one or more echogenic indicator regions associated with at least a portion of the elongated member. The elongated member is configured to be placed within tissue and includes a distal tip. The one or more echogenic indicator regions include one or more heat-sensitive elements adapted to change echogenic properties, when the at least a portion of the elongated member is disposed within tissue, in response to heat generated as a result of energy transmitted to the tissue.

According to another aspect of the present disclosure, an electrosurgical system is provided. The electrosurgical system includes an electrosurgical power generating source, an energy applicator operably associated with the electrosurgical power generating source, a heat-distribution indicator adapted to change echogenic properties in response to heat generated by energy delivered by the energy applicator, a processor unit, and an imaging system capable of acquiring image data. The imaging system is communicatively-coupled to the processor unit. The processor unit is adapted to determine location of margins of ablated tissue relative to target tissue margins based at least in part on analysis of one or more images acquired by the imaging system.

According to another aspect of the present disclosure, a method of directing energy to tissue is provided. The method includes the initial step of determining target tissue location and/or target tissue margins. The method also includes the steps of transmitting energy from an electrosurgical power generating source through an energy applicator to the target tissue, capturing a series of sequential images of at least a portion of the target tissue including data representative of a response of at least one heat-sensitive element of at least one heat-distribution indicator to heat generated by the energy transmitted to the target tissue, analyzing the series of sequential images to assess proximity of margins of ablated tissue to the target tissue margins based at least in part on the response of the at least one heat-sensitive element of the at least one heat-distribution indicator, and determining at least one operating parameter associated with the electrosurgical power generating source based on the proximity of margins of ablated tissue to the target tissue margins.

According to another aspect of the present disclosure, an electrosurgical system is provided. The electrosurgical system includes an electrosurgical power generating source, an energy applicator operably associated with the electrosurgical power generating source, a heat-distribution indicator adapted to change echogenic properties in response to heat generated by energy delivered by the energy applicator, a processor unit, and an imaging system capable of acquiring image data. The imaging system is communicatively-coupled to the processor unit. The processor unit is adapted to determine an ablation rate at least in part based on analysis of one or more images acquired by the imaging system.

According to another aspect of the present disclosure, a method of directing energy to tissue is provided. The method includes the initial steps of determining target tissue location and/or target tissue margins, positioning an energy applicator for delivery of energy to target tissue, and positioning one or more heat-distribution indicators adapted to change echogenic properties in response to heat. The energy applicator is operably associated with an electrosurgical power generating source. The method also includes the steps of transmitting energy from the electrosurgical power generating source through the energy applicator to the target tissue, acquiring data representative of one or more ultrasound images including data representative of a response of one or more heat-sensitive elements of the one or more heat-distribution indicators to heat generated by the energy transmitted to the target tissue, and determining one or more operating parameters associated with the electrosurgical power generating source based on a tissue ablation rate determined based at least in part on the response of the one or more heat-sensitive elements of the one or more heat-distribution indicators.

According to another aspect of the present disclosure, a method of directing energy to tissue is provided. The method includes the initial steps of positioning an energy applicator for delivery of energy to target tissue, and positioning one or more heat-distribution indicators adapted to change echogenic properties in response to heat. The energy applicator is operably associated with an electrosurgical power generating source. The method also includes the steps of transmitting energy from the electrosurgical power generating source through the energy applicator to the target tissue, capturing a series of sequential ultrasound images of at least a portion of the target tissue including data representative of a response of one or more heat-sensitive elements of the one or more heat-distribution indicators to heat generated by the energy transmitted to the target tissue, analyzing the series of sequential ultrasound images to determine a tissue ablation rate based at least in part on the response of the one or more heat-sensitive elements of the one or more heat-distribution indicators, and determining at least one operating parameter associated with the electrosurgical power generating source based on the tissue ablation rate.

In any one of the aspects, the energy applicator may be mechanically-coupled to one or more heat-distribution indicators.

In any one of the aspects, the processor unit is configured to generate at least one electrical signal for controlling one or more operating parameters associated with the electrosurgical power generating source In any one of the aspects, the one or more operating parameters associated with the electrosurgical power generating source may be selected from the group consisting of temperature, impedance, power, current, voltage, mode of operation, and duration of application of electromagnetic energy.

In any one of the aspects, the one or more heat-sensitive elements may be configured to increase in volume and/or decrease in density (or decrease in volume and/or increase in density) when heated to a predetermined temperature or temperature range.

BRIEF DESCRIPTION OF THE DRAWINGS

Objects and features of the presently-disclosed heat-distribution indicators, thermal zone indicators, electrosurgical systems including the same, and methods of directing energy to tissue using the same will become apparent to those of ordinary skill in the art when descriptions of various embodiments thereof are read with reference to the accompanying drawings, of which.

DETAILED DESCRIPTION

Figure 1:
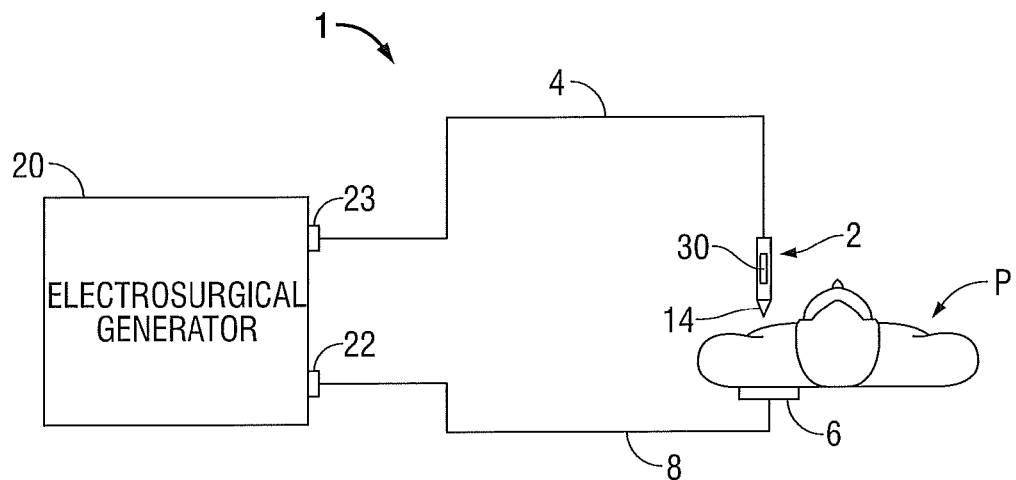
FIG. 1 is a schematic diagram of an electrosurgical system, such as a monopolar electrosurgical system, according to an embodiment of the present disclosure.

Hereinafter, embodiments of the presently-disclosed heat-distribution indicators, thermal zone indicators, electrosurgical devices including the same, and systems and methods for directing energy to tissue are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "transmission line" generally refers to any transmission medium that can be used for the propagation of signals from one point to another.

Various embodiments of the present disclosure provide heat-distribution indicators including one or more heat-sensitive elements configured to change material properties and/or echogenic properties when heated, e.g., to a certain temperature, or temperature range. Various embodiments of the present disclosure provide thermal zone indicators including a thermo-sensitive material, e.g., an irreversible thermochromic dye, configured to change color when heated. In accordance with various embodiments, the use of heat-distribution indicators and/or thermal zone indicators may provide visual feedback, e.g., during real-time ultrasound imaging, while heating, e.g., to allow the surgeon to assess the ablation margins and/or the rate of desiccation of tissue, and/or to adjust, as necessary, the amount of energy delivered to tissue.

Various embodiments of the present disclosure provide electrosurgical systems and instruments suitable for sealing, cauterizing, coagulating/desiccating and/or cutting vessels and vascular tissue, ablating tissue, or otherwise modifying a tissue or organ of a patient, wherein the presently-disclosed heat-distribution indicators allow the surgeon to selectively position the energy applicator in tissue, and/or may allow the surgeon to adjust, as necessary, the amount of energy delivered to tissue to facilitate effective execution of a procedure, e.g., an ablation procedure.

Various embodiments of the presently-disclosed electrosurgical systems and instruments use heat-distribution information provided by the presently-disclosed heat-distribution indicators to assess the ablation margins and/or the rate of desiccation of tissue. Embodiments may be implemented using electromagnetic radiation at RF or microwave frequencies or at other frequencies.

In accordance with embodiments of the present disclosure, one or more operating parameters of an electrosurgical power generating source are adjusted and/or controlled based on the heat-distribution information provided by the presently-disclosed heat-distribution indicators, e.g., to maintain a proper ablation rate, or to determine when tissue has been completely desiccated and/or the procedure has been completed.

Various embodiments of the presently-disclosed electrosurgical systems use heat-distribution information provided by the presently-disclosed heat-distribution indicators to trigger safety procedures and/or controls, e.g., control that reduces power level and/or shuts off the power delivery to the energy applicator, e.g., based on the tissue ablation rate and/or assessment of the ablation margins.

Various embodiments of the presently-disclosed heat-distribution indicator are non-sensitive and/or non-reactive to electromagnetic radiation. Various embodiments of the presently-disclosed heat-distribution indicator allow monitoring of tissue to be performed in real time (e.g., real-time ultrasound monitoring) while heating, e.g., to provide a feedback to control the ablation or other heat treatment procedure.

Although the following description describes the use of electrosurgical systems including a handpiece with an energy applicator adapted for percutaneous energy delivery, the presently-disclosed heat-distribution indicator devices may be used with, mechanically-coupled to, and/or incorporated into any suitable type of handheld medical device or electrosurgical energy delivery device including a handpiece having a surgical instrument, such as, for example, an open device, a catheter-type device, an endoscopic device, and a direct-contact, surface-delivery device.

FIG. 1 schematically illustrates a monopolar electrosurgical system (shown generally as 1) configured to selectively apply electrosurgical energy to target tissue of a patient P. Electrosurgical system 1 generally includes a handpiece 2 coupled via a transmission line 4 to an electrosurgical power generating source 20. Handpiece 2 includes a surgical instrument 14 having one or more electrodes for treating tissue of the patient P (e.g., electrosurgical pencil, electrosurgical cutting probe, ablation electrode(s), etc.). In some embodiments, as shown in FIG. 1, the handpiece 2 includes a control assembly 30. When the electrosurgical energy is applied, the energy travels from the active electrode, to the surgical site, through the patient P and to a return electrode 6 (e.g., a plate positioned on the patient's thigh or back).

Electrosurgical energy is supplied to the instrument 14 by the electrosurgical power generating source 20. Power generating source 20 may be any generator suitable for use with electrosurgical devices to generate energy having a controllable frequency and power level, and may be configured to provide various frequencies of electromagnetic energy. Power generating source 20 may be configured to operate in a variety of modes, such as ablation, monopolar and bipolar cutting, coagulation, and other modes. Control assembly 30 may include a variety of mechanisms adapted to generate signals for adjusting and/or controlling one or more operating parameters (e.g., temperature, impedance, power, current, voltage, mode of operation, and/or duration of application of electromagnetic energy) of the electrosurgical power generating source 20.

The instrument 14 is electrically-coupled via a transmission line, e.g., supply line 4, to an active terminal 23 of the electrosurgical power generating source 20, allowing the instrument 14 to coagulate, ablate and/or otherwise treat tissue. The energy is returned to the electrosurgical power generating source 20 through the return electrode 6 via a transmission line, e.g., return line 8, which is connected to a return terminal 22 of the power generating source 20. In some embodiments, the active terminal 23 and the return terminal 22 may be configured to interface with plugs (not shown) associated with the instrument 14 and the return electrode 6, respectively, e.g., disposed at the ends of the supply line 4 and the return line 8, respectively.

The system 1 may include a plurality of return electrodes 6 that are arranged to minimize the chances of tissue damage by maximizing the overall contact area with the patient P. The power generating source 20 and the return electrode 6 may additionally, or alternatively, be configured for monitoring so-called "tissue-to-patient" contact to ensure that sufficient contact exists therebetween to further minimize chances of tissue damage. The active electrode may be used to operate in a liquid environment, wherein the tissue is submerged in an electrolyte solution.

Figure 2:
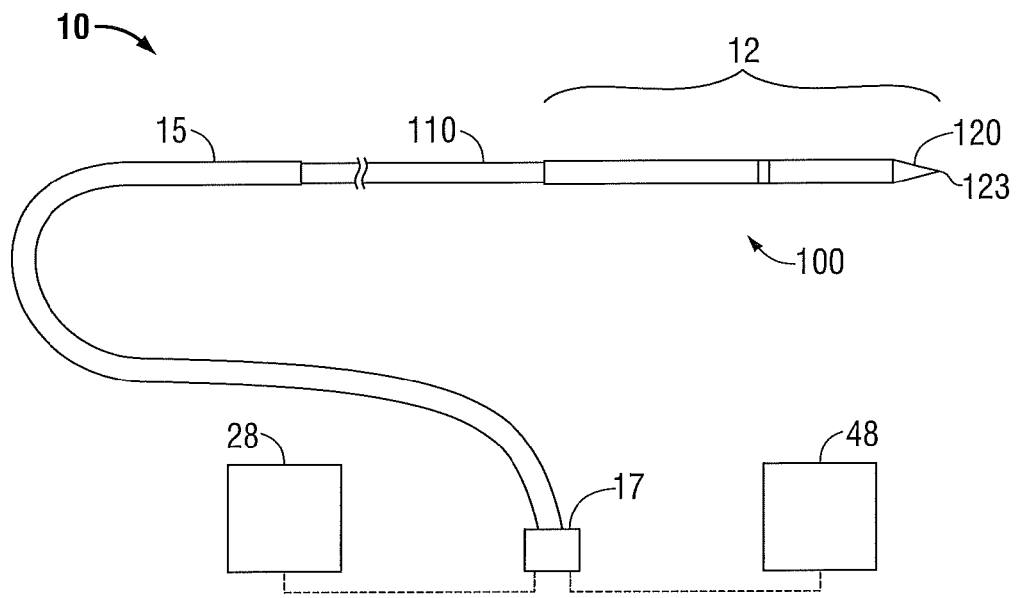
FIG. 2 is a schematic diagram of another embodiment of an electrosurgical system according to the present disclosure.

FIG. 2 schematically illustrates an electrosurgical system (shown generally as 10) including an energy applicator or probe 100. Probe 100 generally includes an antenna assembly 12, and may include a feedline (or shaft) 110 coupled to the antenna assembly 12. Feedline 110 may include a coaxial cable, which may be semi-rigid or flexible. A transmission line 15 may be provided to electrically couple the feedline 110 to an electrosurgical power generating source 28, e.g., a microwave or RF electrosurgical generator.

Feedline 110 may be cooled by fluid, e.g., saline or water, to improve power handling, and may include a stainless steel catheter. Transmission line 15 may additionally, or alternatively, provide a conduit (not shown) configured to provide coolant from a coolant source 18 to the probe 100. In some embodiments, as shown in FIG. 2, the feedline 110 is coupled via a transmission line 15 to a connector 17, which further operably connects the probe 100 to the electrosurgical power generating source 28. Power generating source 28 may be any generator suitable for use with electrosurgical devices, and may be configured to provide various frequencies of energy.

In some embodiments, as shown in FIG. 2, the antenna assembly 12 is a dipole microwave antenna assembly, but other antenna assemblies, e.g., monopole or leaky wave antenna assemblies, may also utilize the principles set forth herein. Located at the distal end of the antenna assembly 12 is an end cap or tapered portion 120, which may terminate in a sharp tip 123 to allow for insertion into tissue with minimal resistance. One example of a straight probe with a sharp tip that may be suitable for use as the energy applicator 100 is commercially available under the trademark EVIDENT™ offered by Covidien Surgical Solutions of Boulder, Colo. The end cap or tapered portion 120 may include other shapes, such as without limitation, a tip 123 that is rounded, flat, square, hexagonal, or cylindroconical.

During microwave ablation, e.g., using the electrosurgical system 10, the probe 100 is inserted into or placed adjacent to tissue and microwave energy is supplied thereto. One or more heat-distribution indicators, which are described in more detail later in this description, may be positioned relative to the probe 100 (and/or relative to a target region). Probe 100 may be placed percutaneously or atop tissue, e.g., using conventional surgical techniques by surgical staff. A clinician may pre-determine the length of time that microwave energy is to be applied. The duration of microwave energy application using the probe 100 may depend on the progress of the heat distribution within the tissue area that is to be destroyed and/or the surrounding tissue.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Ablation volume is correlated with antenna design, antenna performance, number of energy applicators used simultaneously, ablation time and wattage, and tissue characteristics, e.g., tissue impedance.

In operation, microwave energy having a wavelength, lambda ($\lambda$), is transmitted through the antenna assembly 12 and radiated into the surrounding medium, e.g., tissue. The length of the antenna for efficient radiation may be dependent on the effective wavelength, $\lambda_{eff}$, which is dependent upon the dielectric properties of the treated medium. Antenna assembly 12 through which microwave energy is transmitted at a wavelength, $\lambda$, may have differing effective wavelengths, $\lambda_{eff}$, depending upon the surrounding medium, e.g., liver tissue as opposed to breast tissue.

Figure 3A:
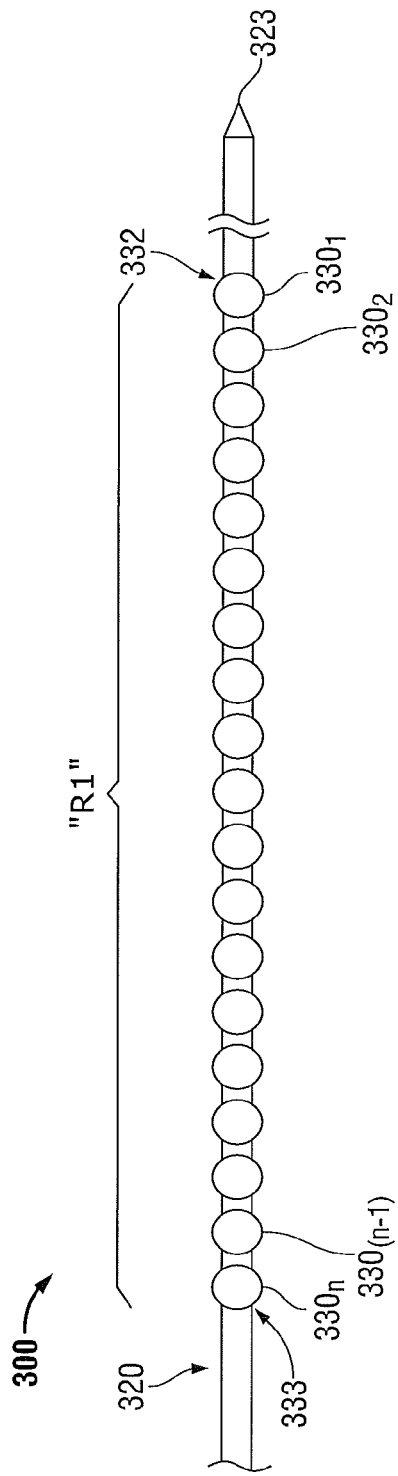
FIG. 3A is a schematic diagram of a heat-distribution indicator including an echogenic indicator region having a plurality of heat-sensitive elements, shown in a first configuration, according to an embodiment of the present disclosure.
Figure 3B:
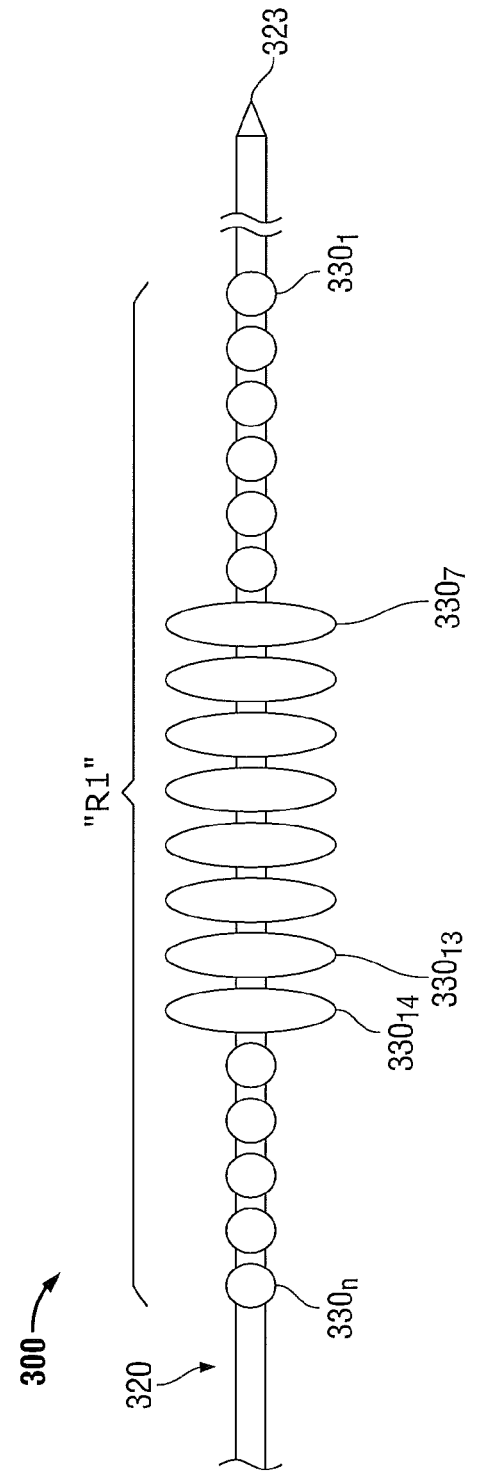
FIG. 3B is a schematic diagram of the heat-distribution indicator of FIG. 3A including the echogenic indicator region thereof shown in a second configuration, such as in response to the application of heat to the heat-sensitive elements thereof during thermal ablation, according to an embodiment of the present disclosure.

In FIGS. 3A and 3B, a heat-distribution indicator (shown generally as 300) according to an embodiment of the present disclosure is shown and includes an elongated member 320 and a configuration of heat-sensitive elements $330_1$-$330_n$ disposed on, or otherwise associated with, at least a portion of the elongated member 320, e.g., echogenic indicator region "R". The echogenic indicator region "R" generally includes a proximal end 333 and a distal end 332 (FIG. 3A), and may include any suitable number n of heat sensitive elements, e.g., $330_1$, $330_2$-$330_{(n-1)}$, $330_n$.

The echogenic indicator region "R" may include any suitable type of heat sensitive element of any suitable material or materials formed by any suitable process. The heat-sensitive elements $330_1$-$330_n$ may be formed of the same or different materials. In alternative embodiments not shown, the echogenic indicator region "R" may include a single heat-sensitive element which may include one or more portions formed of the same or different materials by any suitable process. Heat-distribution indicator 300 may include a handle (not shown) at a proximal end thereof.

One or more heat-sensitive elements $330_1$-$330_n$ may be configured to change material properties and/or echogenic properties when heated to a certain temperature or temperature range. In various embodiments, the heat-sensitive elements $330_1$-$330_n$, may be configured to increase in volume and/or decrease in density (or decrease in volume and/or increase in density) when heated to a predetermined temperature or temperature range, wherein the changes in volume and/or density result in changes in the echogenic properties of the heat-sensitive elements and/or echogenic indicator region(s). As an illustrative, non-limiting example, if certain heat-sensitive elements are formed of material having phase transition (e.g., liquid to gas, or solid to liquid) at a predetermined temperature, e.g., 55° C., the echogenic indicator region "R1", or portions thereof (e.g., heat-sensitive elements $330_7$-$330_{14}$ shown in FIG. 3B) containing those certain heat-sensitive elements will exhibit a phase transition and change in echogenic properties when heated to 55° C. In some embodiments, one or more heat-sensitive elements $330_1$-$330_n$ may be configured to change material properties and/or echogenic properties when heated for at least a predetermined period of time to a certain temperature or temperature range.

In some embodiments, the heat-sensitive elements $330_1$-$330_n$ may be fixed relative to one another, relative to the proximal end 333 and the distal end 332 of the echogenic indicator region "R", and/or relative to a fixed point on the elongated member 320, e.g., distal tip 323 thereof. The locations of the heat-sensitive elements $330_1$-$330_n$ may be mapped to a suitable coordinate system, e.g., to facilitate image processing of images including data representative of one or more heat-sensitive elements, one or more echogenic indicator regions, or portions thereof (e.g., first portion "P1", second portion "P2" and/or third portion "P3" of echogenic indicator region "R2" shown in FIG. 3C). In some embodiments, the mapping of the heat-sensitive elements $330_1$-$330_n$ may be based on their center points, e.g., relative to the distal tip 323 of the elongated member (e.g., 320 shown in FIGS. 3A-3C or 420 shown in FIG. 3D).

Figure 3C:
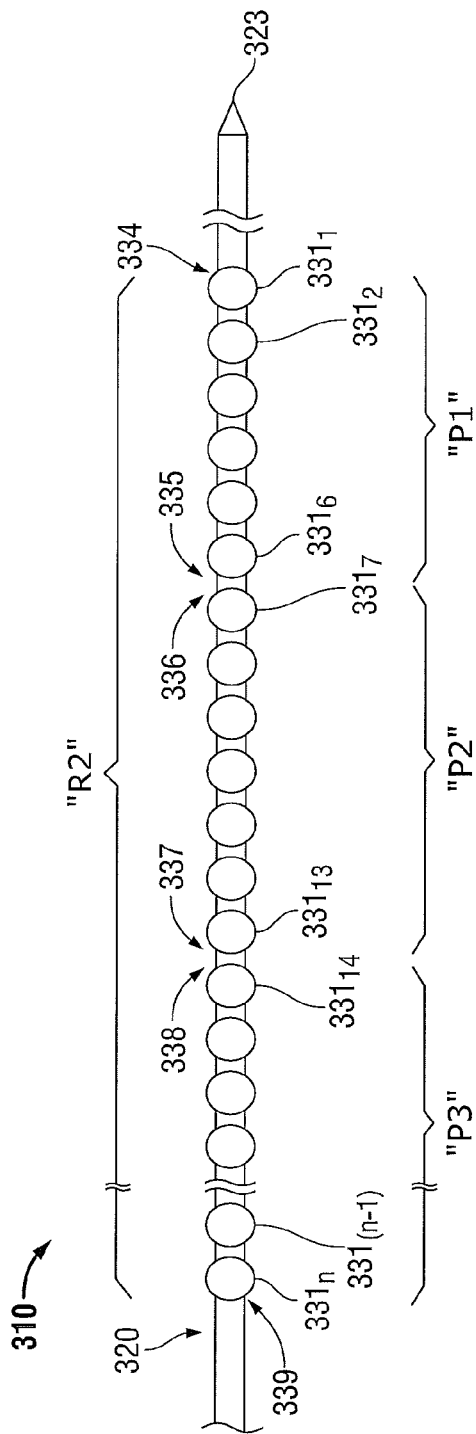
FIG. 3C is a schematic diagram of a heat-distribution indicator including an echogenic indicator region having a plurality of heat-sensitive elements according to another embodiment of the present disclosure.

In FIG. 3C, a heat-distribution indicator (shown generally as 310) according to an embodiment of the present disclosure is shown and includes the elongated member 320 of FIG. 3A and a configuration of heat-sensitive elements $331_1$-$331_n$ disposed on, or otherwise associated with, at least a portion of the elongated member 320, e.g., echogenic indicator region "R2". Heat-distribution indicator 310 may include a handle (not shown) at a proximal end thereof.

In some embodiments, as shown in FIG. 3C, the echogenic indicator region "R2" includes a first portion "P1" having a proximal end 335 and a distal end 334, a second portion "P2" having a proximal end 337 and a distal end 336, and a third portion "P3" having a proximal end 339 and a distal end 338. The first portion "P1" includes a plurality of heat-sensitive elements, e.g., six elements $331_1$-$331_6$, formed of a first material configured to change material properties and/or echogenic properties when heated to a first predetermined temperature or temperature range. The second portion "$P_2$" includes a plurality of heat-sensitive elements, e.g., seven elements $331_7$-$331_{13}$, formed of a second material configured to change material properties and/or echogenic properties when heated to a second predetermined temperature or temperature range. The third portion "$P_3$" may include any suitable number n of heat-sensitive elements $331_{14}$-$331_{(n-1)}$, $330_n$ formed of a third material configured to change material properties and/or echogenic properties when heated to a third predetermined temperature or temperature range. The first, second and third predetermined temperatures (or temperature ranges) may be any suitable temperatures (or temperature ranges).

Figure 3D:
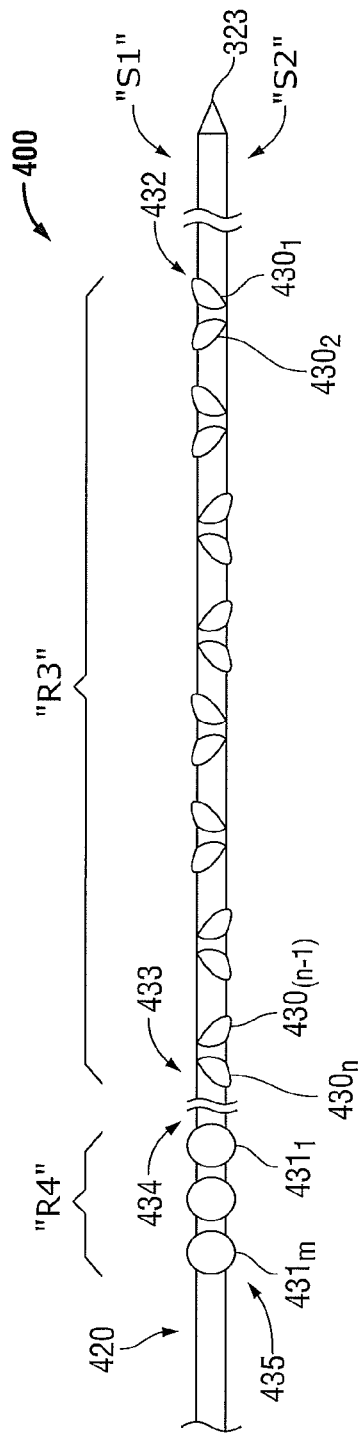
FIG. 3D is a schematic diagram of a heat-distribution indicator including two echogenic indicator regions according to an embodiment of the present disclosure.

In FIG. 3D, a heat-distribution indicator (shown generally as 400) according to an embodiment of the present disclosure is shown and includes an elongated member 420, a first echogenic indicator region "R3" including a number n of heat-sensitive elements $430_1$, $430_2$-$430_{(n-1)}$, $430_n$ disposed on, or otherwise associated with, a portion of the elongated member 420 having a proximal end 433 and a distal end 432, and a second echogenic indicator region "R4" including a number m of heat-sensitive elements $431_1$-$431_m$ disposed on, or otherwise associated with, a second portion of the elongated member 420 having a proximal end 435 and a distal end 434. The elongated member 420 is similar to the elongated member 320 shown in FIGS. 3A-3C and further description thereof is omitted in the interests of brevity.

Figure 4A:
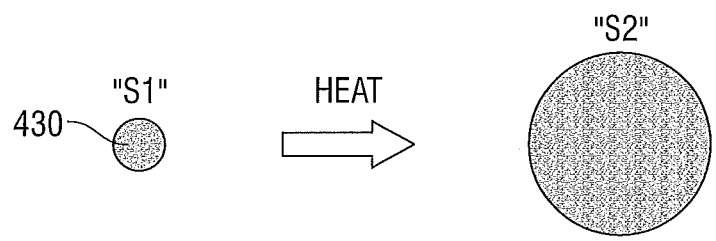
FIG. 4A is a diagrammatic representation of a first type of modification and/or transformation of the echogenic properties of a heat sensitive element, such as a heat sensitive element of the heat-distribution indicator of FIG. 3A, according to an embodiment of the present disclosure.
Figure 4B:
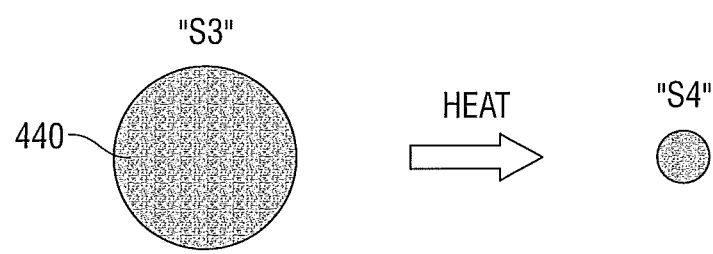
FIG. 4B is a diagrammatic representation of a second type of modification and/or transformation of the echogenic properties of a heat sensitive element, such as a heat sensitive element of the heat-distribution indicator of FIG. 3A, according to an embodiment of the present disclosure.
Figure 4C:
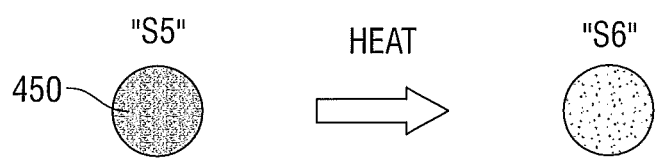
FIG. 4C is a diagrammatic representation of a third type of modification and/or transformation of the echogenic properties of a heat sensitive element, such as a heat sensitive element of the heat-distribution indicator of FIG. 3A, according to an embodiment of the present disclosure.
Figure 4D:
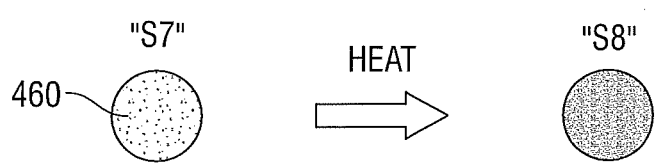
FIG. 4D is a diagrammatic representation of a fourth type of modification and/or transformation of the echogenic properties of a heat sensitive element, such as a heat sensitive element of the heat-distribution indicator of FIG. 3A, according to an embodiment of the present disclosure.

In some embodiments, as shown in FIG. 4D, the heat-sensitive elements $430_1$-$430_n$ are configured as pairs, e.g., $430_1$, $430_2$, and configured in an alternating pattern relative to the opposite lateral sides "S1", "S2" of the elongated member 420, e.g., to allow assessment of heat distribution on the opposite lateral sides "S1", "S2 of the elongated member 420 such as when heated to a first predetermined temperature or temperature range.

Figure 5:
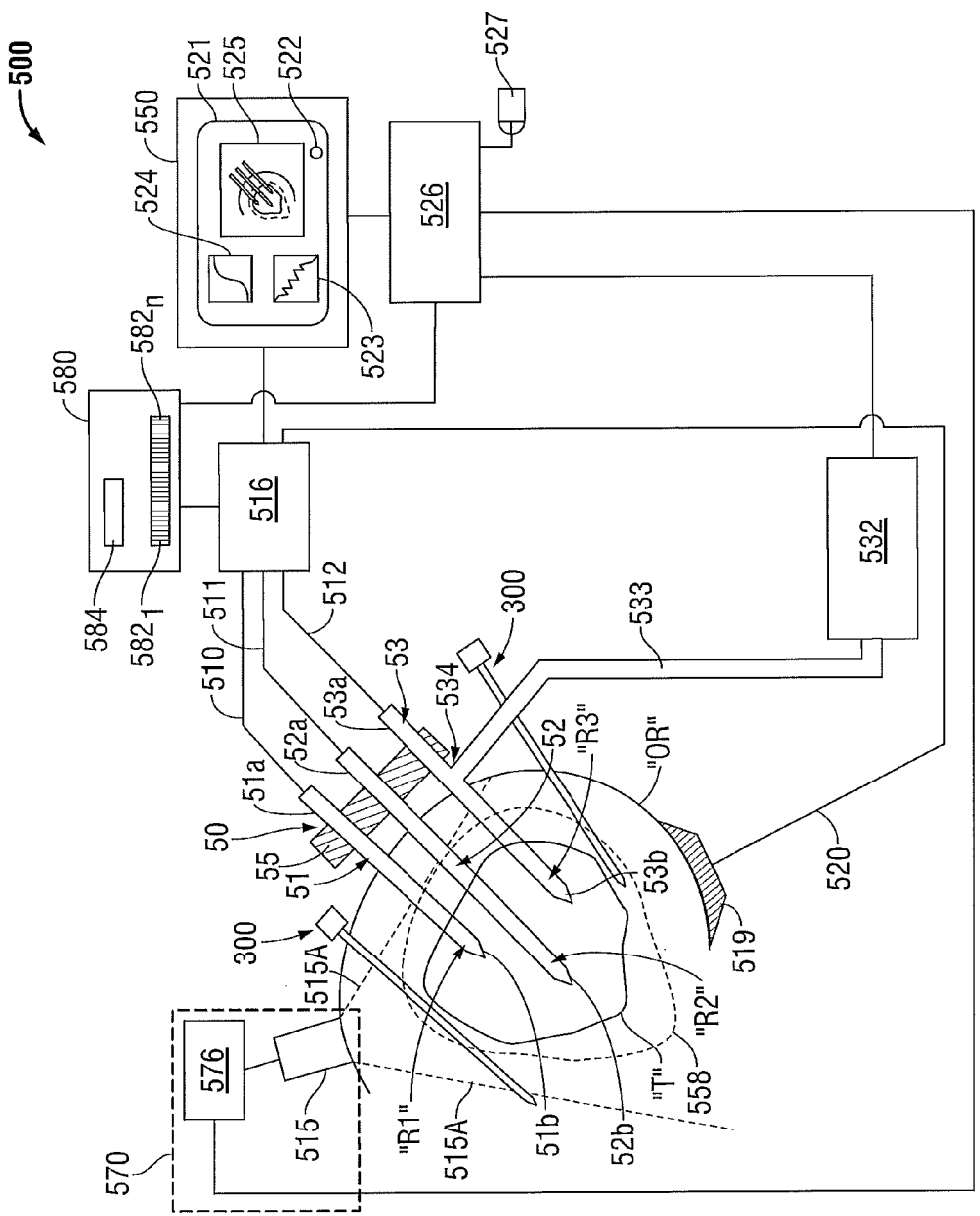
FIG. 5 is a schematic diagram of an electrosurgical system including the heat-distribution indicator of FIG. 3A shown with an energy applicator array positioned for the delivery of energy to target tissue according to an embodiment of the present disclosure.
Figure 6:
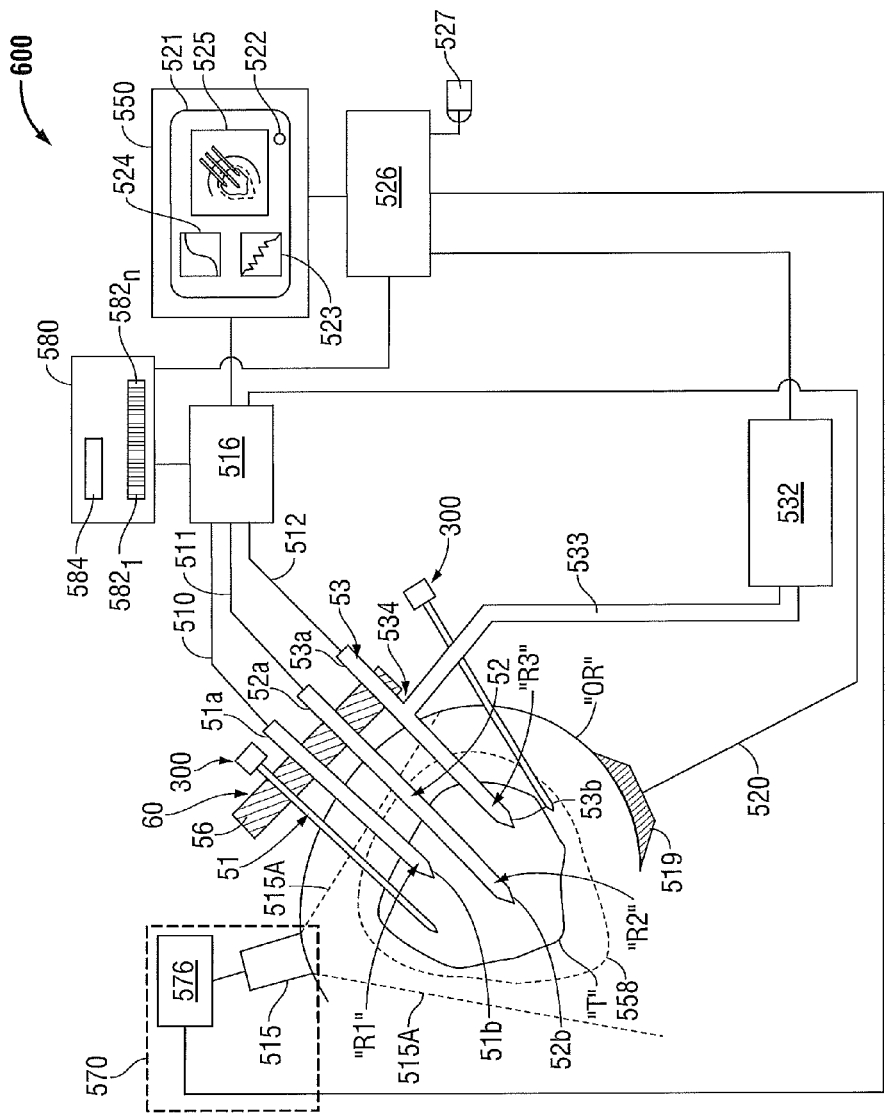
FIG. 6 is a schematic diagram of an electrosurgical system similar to the electrosurgical system of FIG. 5, except for the configuration of the energy delivery device, according to an embodiment of the present disclosure.

Parameters associated with the heat-distribution indicators (e.g., 300, 310 and 400 shown in FIGS. 3A-3D), such as the material properties and/or echogenic properties, the configuration of heat-sensitive elements associated with a particular echogenic indicator region (e.g., "R1", "R2", "R3" and "R4" shown in FIGS. 3A-3D), and/or the mapping of the heat-sensitive elements of the echogenic indicator region(s) of the heat-distribution indicators may be stored in a database (e.g., 584 shown in FIGS. 5 and 6).

A change in the echogenic properties of one or more heat-sensitive elements typically will result in a change in the acoustic wave reflection in the echogenic indicator region "R1", "R2", "R3" and/or "R4", or portions thereof, containing the one or more heat-sensitive elements which may appear brighter, or darker, on ultrasound imaging. In some embodiments, a heat sensitive element that reflects a large amount of sound energy will appear brighter on an ultrasound image, and/or a display device (or screen), as compared to less reflective heat-sensitive elements which appear darker. In some embodiments, image data including ultrasound images (and/or images from other modalities) representative of tissue and the heat-distribution indicator 300, 310 and/or 400 and/or echogenic indicator region "R1", "R2", "R3" and/or "R4" thereof may be stored in and retrievable from a library, e.g., for subsequent use in controlling an ablation procedure, as described in more detail later in this description.

The elongated member 320 may be formed of a suitable material, such as a flexible, semi-rigid or rigid material. The heat-distribution indicator 300 thickness may be minimized, e.g., to reduce trauma to the surgical site and/or facilitate accurate placement of the device 300 to allow surgeons to treat and/or monitor target tissue with minimal damage to surrounding healthy tissue.

The visual assistance provided by the heat-sensitive elements $330_1$-$330_n$ may allow the surgeon to selectively position the energy applicator (e.g., probe 100 shown in FIG. 2) in tissue, and/or may allow the surgeon to monitor and adjust, as necessary, the amount of energy delivered to tissue. In some embodiments, as shown in FIGS. 5 and 6, the change in the acoustic wave reflection in the echogenic indicator region "R1", or portions thereof, permits for systems for automated feedback control of one or more parameters associated with an energy delivery device and/or one or more parameters associated with an electrosurgical power generating source, such as to facilitate effective execution of a procedure, e.g., an ablation procedure.

FIG. 5 schematically illustrates an electrosurgical system (shown generally as 500) according to an embodiment of the present disclosure that includes an electromagnetic energy delivery device or energy applicator array 50 positioned for the delivery of energy to a target region "T". Energy applicator array 50 may include one or more energy applicators or probes.

In some embodiments, as shown in FIG. 5, the electrosurgical system 500 includes two heat-distribution indicators 300. It is to be understood that any suitable number of heat-distribution indicators 300 may be used. In some embodiments, one or more heat-distribution indicators may additionally, or alternatively, be mechanically-coupled to the energy delivery device or component thereof (e.g., support member 56 of the energy delivery device 60 shown in FIG. 6). The relative positioning of the heat-distribution indicators 300 may be varied from the configuration depicted in FIG. 5.

In the embodiment shown in FIG. 5, the energy applicator array 50 includes three probes 51, 52 and 53 having different lengths and arranged substantially parallel to each other. The probes may have similar or different diameters, may extend to equal or different lengths, and may have a distal end with a tapered tip. In some embodiments, the probe(s) may be provided with a coolant chamber, and may be integrally associated with a hub (e.g., hub 534 shown in FIG. 5) that provides electrical and/or coolant connections to the probe(s). Additionally, or alternatively, the probe(s) may include coolant inflow and outflow ports to facilitate the flow of coolant into, and out of, the coolant chamber.

Probes 51, 52 and 53 generally include a radiating section "R1", "R2" and "R3", respectively, operably connected by a feedline (or shaft) 51a, 52a and 53a, respectively, to an electrosurgical power generating source 516, e.g., a microwave or RF electrosurgical generator. In some embodiments, the power generating source 516 is configured to provide microwave energy at an operational frequency from about 300 MHz to about 10 GHz. Power generating source 516 may be configured to provide various frequencies of electromagnetic energy.

Transmission lines 510, 511 and 512 may be provided to electrically couple the feedlines 51a, 52a and 53a, respectively, to the electrosurgical power generating source 516. Located at the distal end of each probe 51, 52 and 53 is a tip portion 51b, 52b and 53b, respectively, which may be configured to be inserted into an organ "OR" of a human body or any other body tissue. Tip portion 51b, 52b and 53b may terminate in a sharp tip to allow for insertion into tissue with minimal resistance. The shape, size and number of probes of the energy applicator array 50 may be varied from the configuration depicted in FIG. 5.

Electrosurgical system 500 according to embodiments of the present disclosure includes a user interface 550. User interface 550 may include a display device 521, such as without limitation a flat panel graphic LCD (liquid crystal display), adapted to visually display one or more user interface elements (e.g., 523, 524 and 525 shown in FIG. 5). In an embodiment, the display device 521 includes touch-screen capability, e.g., the ability to receive user input through direct physical interaction with the display device 521, e.g., by contacting the display panel of the display device 521 with a stylus or fingertip. A user interface element (e.g., 523, 524 and/or 525 shown in FIG. 5) may have a corresponding active region, such that, by touching the display panel within the active region associated with the user interface element, an input associated with the user interface element is received by the user interface 550.

User interface 550 may additionally, or alternatively, include one or more controls 522 that may include without limitation a switch (e.g., pushbutton switch, toggle switch, slide switch) and/or a continuous actuator (e.g., rotary or linear potentiometer, rotary or linear encoder). In an embodiment, a control 522 has a dedicated function, e.g., display contrast, power on/off, and the like. Control 522 may also have a function that may vary in accordance with an operational mode of the electrosurgical system 500. A user interface element (e.g., 523 shown in FIG. 5) may be provided to indicate the function of the control 522.

As shown in FIG. 5, the electrosurgical system 500 may include a reference electrode 519 (also referred to herein as a "return" electrode). Return electrode 519 may be electrically coupled via a transmission line 520 to the power generating source 516. During a procedure, the return electrode 519 may be positioned in contact with the skin of the patient or a surface of the organ "OR". When the surgeon activates the energy applicator array 50, the return electrode 519 and the transmission line 520 may serve as a return current path for the current flowing from the power generating source 516 through the probes 51, 52 and 53.

During microwave ablation, e.g., using the electrosurgical system 100, the energy applicator array 50 is inserted into or placed adjacent to tissue and microwave energy is supplied thereto. Ultrasound or computed tomography (CT) guidance may be used to accurately guide the energy applicator array 50 into the area of tissue to be treated. A clinician may pre-determine the length of time that microwave energy is to be applied. Application duration may depend on a variety of factors such as energy applicator design, number of energy applicators used simultaneously, tumor size and location, and whether the tumor was a secondary or primary cancer. The duration of microwave energy application using the energy applicator array 50 may depend on the progress of the heat distribution within the tissue area that is to be destroyed and/or the surrounding tissue.

FIG. 5 shows a target region including ablation target tissue represented in sectional view by the solid line "T". It may be desirable to ablate the target region "T" by fully engulfing the target region "T" in a volume of lethal heat elevation. Target region "T" may be, for example, a tumor that has been detected by a medical imaging system 530.

Medical imaging system 530, according to various embodiments, includes one or more image acquisition devices (e.g., scanner 515 shown in FIG. 5) of any suitable imaging modality. Medical imaging system 530 may additionally, or alternatively, include a medical imager (not shown) operable to form a visible representation of the image based on the input pixel data. Medical imaging system 530 may include a computer-readable storage medium such as an internal memory unit 576, which may include an internal memory card and removable memory, capable of storing image data representative of an ultrasound image (and/or images from other modalities) received from the scanner 515. In some embodiments, the medical imaging system 530 may be a multi-modal imaging system capable of scanning using different modalities. Examples of imaging modalities that may be suitably and selectively used include X-ray systems, ultrasound (UT) systems, magnetic resonance imaging (MRI) systems, computed tomography (CT) systems, single photon emission computed tomography (SPECT), and positron emission tomography (PET) systems.

Medical imaging system 530, according to embodiments of the present disclosure, may include any device capable of generating digital data representing an anatomical region of interest. Medical imaging system 530 may be a multi-modal imaging system capable of scanning tissue in a first modality to obtain first modality data and a second modality to obtain second modality data, wherein the first modality data and/or the second modality data includes image data representative of tissue and one or more of the presently-disclosed heat-distribution indicators and/or echogenic indicator region "R1" thereof.

Image data representative of one or more images may be communicated between the medical imaging system 530 and a processor unit 526. Medical imaging system 530 and the processor unit 526 may utilize wired communication and/or wireless communication. Processor unit 526 may include any type of computing device, computational circuit, or any type of processor or processing circuit capable of executing a series of instructions that are stored in a computer-readable storage medium (not shown), which may be any device or medium that can store code and/or data. Processor unit 526 may be adapted to run an operating system platform and application programs. Processor unit 526 may receive user inputs from a keyboard (not shown), a pointing device 527, e.g., a mouse, joystick or trackball, and/or other device communicatively-coupled to the processor unit 526.

Medical imaging system 530 and/or the processor unit 526 may be adapted to perform image analysis. Image analysis methods according to embodiments of the present disclosure may include thresholding to segment image data by setting all pixels whose intensity values are above a predetermined threshold to a foreground value and all the remaining pixels to a background value. Thresholding may produce a segmentation that yields substantially all the pixels that belong to the object of interest in the image data. Thresholding may be applied to an entire image, or may be used on a region by region basis.

As shown in FIG. 5, a scanner 515 of any suitable imaging modality may be disposed in contact with the organ "OR" to provide image data. As an illustrative example, the two dashed lines 515A in FIG. 5 bound a region for examination by the scanner 515, e.g., a real-time ultrasonic scanner.

In FIG. 5, the dashed line 558 surrounding the target region "T" represents the ablation isotherm in a sectional view through the organ "OR". Such an ablation isotherm may be that of the surface achieving possible temperatures of approximately 50° C. or greater. The shape and size of the ablation isotherm volume, as illustrated by the dashed line 558, may be influenced by a variety of factors including the configuration of the energy applicator array 50, the geometry of the radiating sections "R1", "R2" and "R3", cooling of the probes 51, 52 and 53, ablation time and wattage, and tissue characteristics.

Processor unit 526 may be connected to one or more display devices (e.g., 521 shown in FIG. 5) for displaying output from the processor unit 26, which may be used by the clinician to visualize the target region "T", the ablation isotherm volume 558, and/or the ablation margins in real-time, or near real-time, during a procedure, e.g., an ablation procedure.

In embodiments, real-time data and/or near real-time data acquired from CT scan, ultrasound, or MRI (or other scanning modality) that includes heat-distribution information, e.g., data representative of one or more heat-distribution indicators and/or echogenic indicator region "R1" thereof during an ablation procedure, may be outputted from the processor unit 526 to one or more display devices. Processor unit 526 is adapted to analyze image data including heat-distribution information to determine one or more parameters associated with the energy applicator array 50 and/or one or more parameters associated with the electrosurgical power generating source 516 e.g., based on the tissue ablation rate and/or assessment of the ablation margins. Visualization of heat distribution from the electrode or antenna as it is being used in the patient may allow detection of the beginning of a non-uniform ablation field.

In some embodiments, the patient's anatomy may be scanned by one or more of several scanning modalities, such as CT scanning, MRI scanning, ultrasound, PET scanning, etc., so as to visualize the tumor and the surrounding normal tissue. The tumor dimensions may thereby be determined and/or the location of the tumor relative to critical structures and the external anatomy may be ascertained. An optimal number and size of energy applicators might be selected so that the ablation isotherms can optimally engulf and kill the tumor with a minimal number of electrode insertions and minimal damage to surrounding healthy tissue.

Electrosurgical system 500 may include a library 580 including a plurality of heat-distribution indicator (and/or echogenic indicator region "R1", "R2", "R3") profiles or overlays $582_1$-$582_n$. As it is used in this description, "library" generally refers to any repository, databank, database, cache, storage unit and the like. Each of the overlays $582_1$-$582_n$ may include a thermal profile that is characteristic of and/or specific to particular heat sensitive element configurations (e.g., heat-sensitive elements $330_1$-$330_n$ of the echogenic indicator region "R1" shown in FIG. 3B), particular heat-distribution indicator designs (e.g., heat-distribution indicator 300 shown in FIGS. 3A and 3B, heat-distribution indicator 310 shown in FIG. 3C, and/or heat-distribution indicator 400 shown in FIG. 3D), and/or exposure time.

Library 580 according to embodiments of the present disclosure may include a database 584 that is configured to store and retrieve energy applicator data, e.g., parameters associated with one or more energy applicators (e.g., 51, 52 and 53 shown in FIG. 5) and/or one or more energy applicator arrays (e.g., 50 shown in FIG. 5) and/or parameters (e.g., echogenicity data) associated with one or more heat-distribution indicators and/or echogenic indicator region thereof (e.g., "R1", "R2" and "R3" shown in FIGS. 3A-3D). Parameters stored in the database 584 in connection with an energy applicator, or an energy applicator array, may include, but are not limited to, energy applicator (or energy applicator array) identifier, energy applicator (or energy applicator array) dimensions, a frequency, an ablation length (e.g., in relation to a radiating section length), an ablation diameter, a temporal coefficient, a shape metric, and/or a frequency metric. In an embodiment, ablation pattern topology may be included in the database 584, e.g., a wireframe model of an energy applicator array (e.g., 525 shown in FIG. 5) and/or a representation of a radiation pattern associated therewith.

Images and/or non-graphical data stored in the library 580, and/or retrievable from a PACS database (not shown), may be used to configure the electrosurgical system 500 and/or control operations thereof. For example, heat-distribution information, e.g., data representative of one or more heat-distribution indicators and/or echogenic indicator region "R1", "R2" and/or "R3" thereof during an ablation procedure, according to embodiments of the present disclosure, may be used as a feedback tool to control an instrument's and/or clinician's motion, e.g., to allow clinicians to avoid ablating certain structures, such as large vessels, healthy organs or vital membrane barriers.

Images and/or non-graphical data stored in the library 580, and/or retrievable from a PACS database (not shown), may be used to facilitate planning and effective execution of a procedure, e.g., an ablation procedure. Heat-distribution information, e.g., data representative of one or more heat-distribution indicators and/or echogenic indicator region "R1", "R2" and/or "R3" thereof (prior to and/or during an ablation procedure), according to embodiments of the present disclosure, may be used as a predictive display of how an ablation will occur prior to the process of ablating. Images and/or heat distribution information displayed on the display device 21 of the user interface 50, for example, may be used by the clinician to better visualize and understand how to achieve more optimized results during thermal treatment of tissue, such as, for example, ablation of tissue, tumors and cancer cells e.g., based on the tissue ablation rate and/or assessment of the ablation margins.

FIG. 6 schematically illustrates an electrosurgical system (shown generally as 600) according to an embodiment of the present disclosure that is similar to the electrosurgical system 500 of FIG. 5, except for the configuration of the electromagnetic energy delivery device (or energy applicator array) 60, and further description of the same components as those of the electrosurgical system of FIG. 5 is omitted in the interests of brevity.

Energy applicator array 60 includes the probes 51, 52 and 53 of FIG. 5 and a support member 56 configured to provide support to the probes 51, 52 and 53. Support member 56 is similar to the support member 55 of the energy applicator array 50 shown in FIG. 5, except that the support member 56 of FIG. 6 is configured to support a heat-distribution indicator 300. In some embodiments, the heat-distribution indicator 300 may be removeably coupleable to the support member 56. In alternative embodiments not shown, the support member 56 may be configured to support a plurality of heat-distribution indicators 300, which may be positioned at any of a variety of locations relative to the probes 51, 52 and 53.

Figure 7:
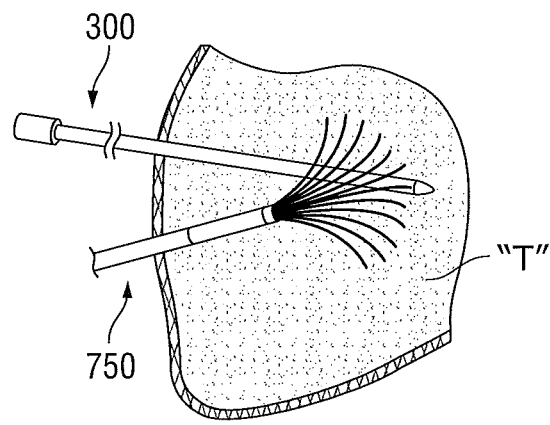
FIG. 7 is a schematic diagram of the heat-distribution indicator of FIG. 3A shown with an energy delivery device positioned for delivery of energy to a tissue region, shown in cross section, according to an embodiment of the present disclosure.

In FIG. 7, the heat-distribution indicator 300 of FIG. 3A is shown positioned in proximity to an energy delivery device 750 positioned for delivery of energy to a region of tissue "T". A variety of medical imaging modalities, e.g., computed tomography (CT) scan or ultrasound, may be used to guide the energy delivery device 750 and/or the heat-distribution indicator 300 into the area of tissue "T" to be treated.

Figure 8A:
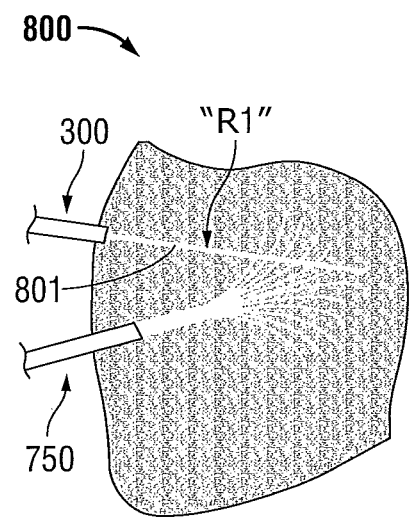
FIG. 8A is a diagrammatic representation of an ultrasound image showing the tissue cross section of FIG. 7 with the heat-distribution indicator in the first configuration shown in FIG. 3A, such as prior to delivery of energy to tissue, according to an embodiment of the present disclosure.

FIG. 8A diagrammatically illustrates an ultrasound image 800 of the tissue region shown in FIG. 7, e.g., prior to delivery of energy thereto, wherein the echogenic indicator region "R1" of the heat-distribution indicator 300 is configured in the first configuration (FIG. 3A) and appears as a bright white band 801 on the ultrasound image 800 or screen (e.g., display device 521 shown in FIG. 5). In some embodiments, when the echogenic indicator region "R1" is configured in the first configuration, the bright/echogenic band 801 indicative of the heat-distribution indicator 300 may be a smooth, linear band of substantially uniform width. In alternative embodiments not shown, the configuration of the one or more bright/echogenic bands indicative of the heat-distribution indicator on an image (e.g., ultrasound image) may vary in width, contour smoothness, and/or brightness, e.g., depending on the material properties and/or echogenic properties of the one or more heat-sensitive elements and/or the one or more echogenic indicator regions of the particular heat-distribution indicator.

Figure 8B:
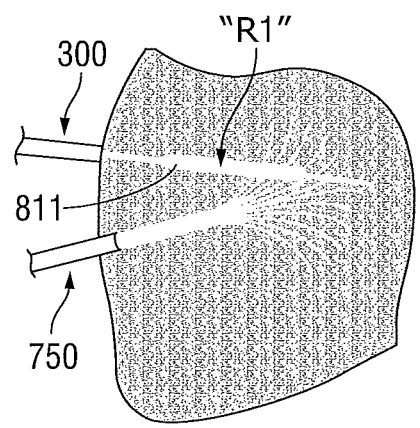
FIG. 8B is a diagrammatic representation of an ultrasound image showing the tissue cross section of FIG. 7 with the heat-distribution indicator shown in a modified configuration, such as responsive to thermal ablation, according to an embodiment of the present disclosure.

FIG. 8B is a diagrammatic representation of an ultrasound image showing the tissue region of FIG. 7 with the echogenic indicator region "R1" of the heat-distribution indicator 300 shown in a modified configuration, e.g., responsive to thermal ablation. In some embodiments, as shown in FIG. 8B, the width of the bright/echogenic band 811 indicative of the echogenic indicator region "R1", e.g., responsive to heat, appears larger on the ultrasound image, relative to the width of the band 801 indicative of the heat-distribution indicator 300, e.g., prior to delivery of energy thereto, shown in FIG. 8A.

Hereinafter, methods of directing energy to tissue are described with reference to FIGS. 9, 10 and 16. It is to be understood that the steps of the methods provided herein may be performed in combination and in a different order than presented herein without departing from the scope of the disclosure.

Figure 9:
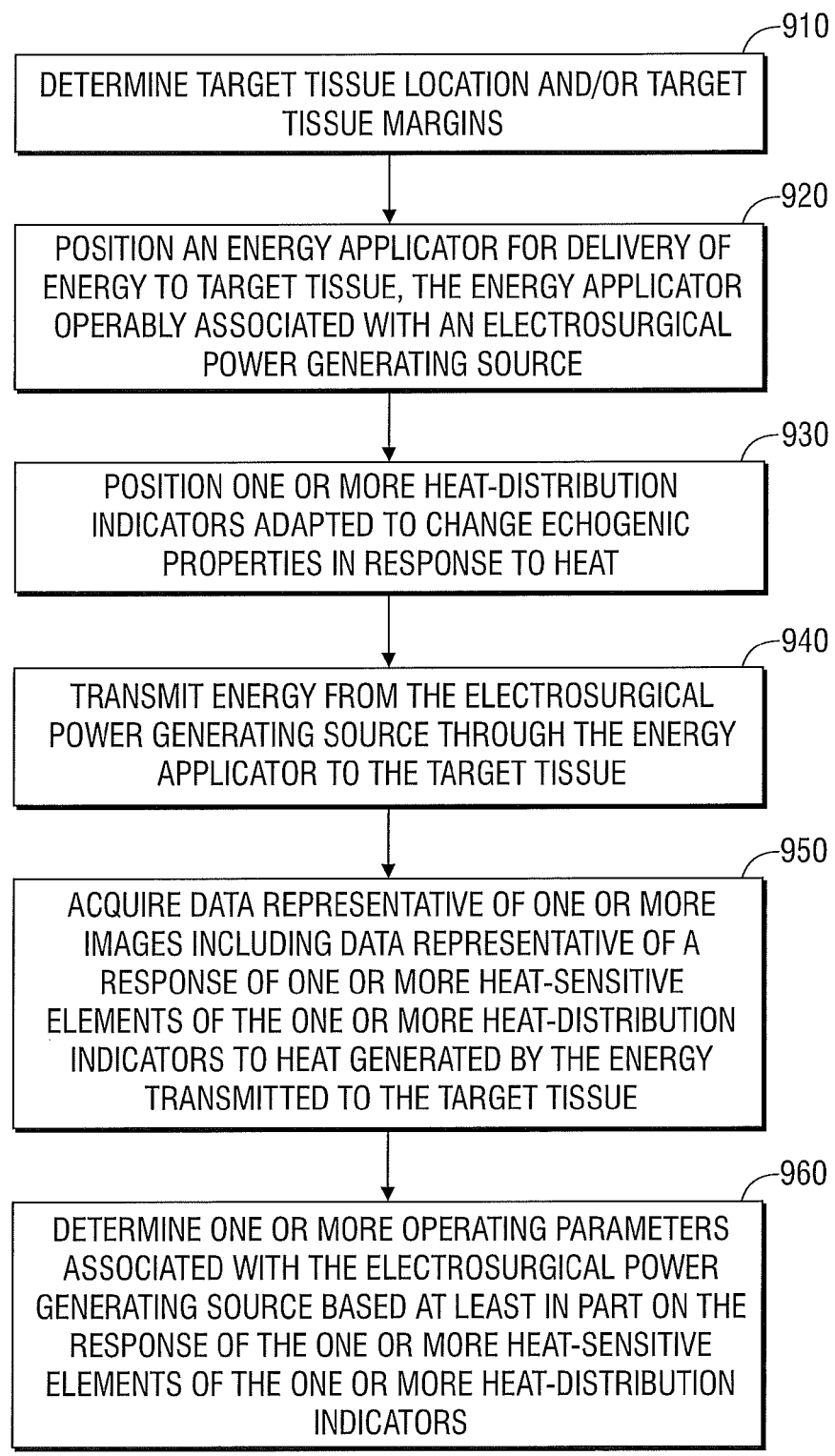
FIG. 9 is a flowchart illustrating a method of directing energy to tissue in accordance with an embodiment of the present disclosure.

FIG. 9 is a flowchart illustrating a method of directing energy to tissue according to an embodiment of the present disclosure. In step 910, target tissue "T" location and/or target tissue "T" margins are determined.

In step 920, an energy applicator 60 is positioned for delivery of energy to target tissue "T". The energy applicator may be inserted directly into tissue "T", inserted through a lumen, e.g., a vein, needle or catheter, placed into the body during surgery by a clinician, or positioned in the body by other suitable methods. Ultrasound or CT guidance may be used to guide the energy applicator 60 into the area of tissue "T" to be treated. The energy applicator 60 is operably associated with an electrosurgical power generating source 516.

Step 920 may include positioning one or more heat-distribution indicators 300 including one or more heat-sensitive elements $330_1$-$330_n$ adapted to change echogenic properties in response to heat. In some embodiments, the energy applicator 60 may be mechanically-coupled to one or more heat-distribution indicators 300.

In step 930, one or more heat-distribution indicators 300 are positioned. The one or more heat-distribution indicators 300 each include one or more heat-sensitive elements $330_1$-$330_n$ adapted to change echogenic properties in response to heat.

In step 940, energy from the electrosurgical power generating source 516 is transmitted through the energy applicator 60 to the target tissue "T". The electrosurgical power generating source 516 may be capable of generating energy at RF or microwave frequencies or at other frequencies.

In step 950, data is acquired representative of one or more images 800 including data representative of the response of one or more heat-sensitive elements $330_1$-$330_n$ of the one or more heat-distribution indicators 300 to heat generated by the energy transmitted to the target tissue "T" by the energy applicator 60. Acquiring data representative of one or more images, in step 950, may include acquiring at one or more ultrasound images using a real-time ultrasonic scanner, and acquiring one or more ultrasound images from a database.

In step 960, one or more operating parameters associated with the electrosurgical power generating source 516 are determined based at least in part on the response of the one or more heat-sensitive elements $330_1$-$330_n$ of the one or more heat-distribution indicators 300. Determining one or more operating parameters associated with the electrosurgical power generating source 516, in step 960, may include determining a tissue ablation rate and determining one or more operating parameters associated with the electrosurgical power generating source 516 based at least in part on the determined tissue ablation rate. Some examples of operating parameters associated with an electrosurgical power generating source 516 that may be determined include temperature, impedance, power, current, voltage, mode of operation, and duration of application of electromagnetic energy.

The tissue ablation rate may be determined based at least in part on the response of the one or more heat-sensitive elements $330_1$-$330_n$ of the one or more heat-distribution indicators 300. The tissue ablation rate may be determined by a processor unit 526 adapted to determine the location of margins of ablated tissue based at least in part on analysis of one or more images 800, 810 acquired by an imaging system 530 communicatively-coupled to the processor unit 526. The determination of the location of the margins of the ablated tissue may involve any suitable computer-implemented image segmentation method. In some embodiments, the position of the energy applicator (e.g., probes 51, 52 and/or 53 shown in FIGS. 5 and 6) may be adjusted based at least in part on the location of the margins of the ablated tissue.

In some embodiments, the position of the energy applicator (e.g., probes 51, 52 and/or 53 shown in FIGS. 5 and 6) may be adjusted based on the tissue ablation rate. In alternative embodiments not shown, an energy applicator with a directional radiation pattern may be rotated either manually, or automatically, based on the tissue ablation rate and/or assessment of the ablation margins, e.g., to avoid ablating sensitive structures, such as large vessels, healthy organs or sensitive membrane barriers.

Figure 10:
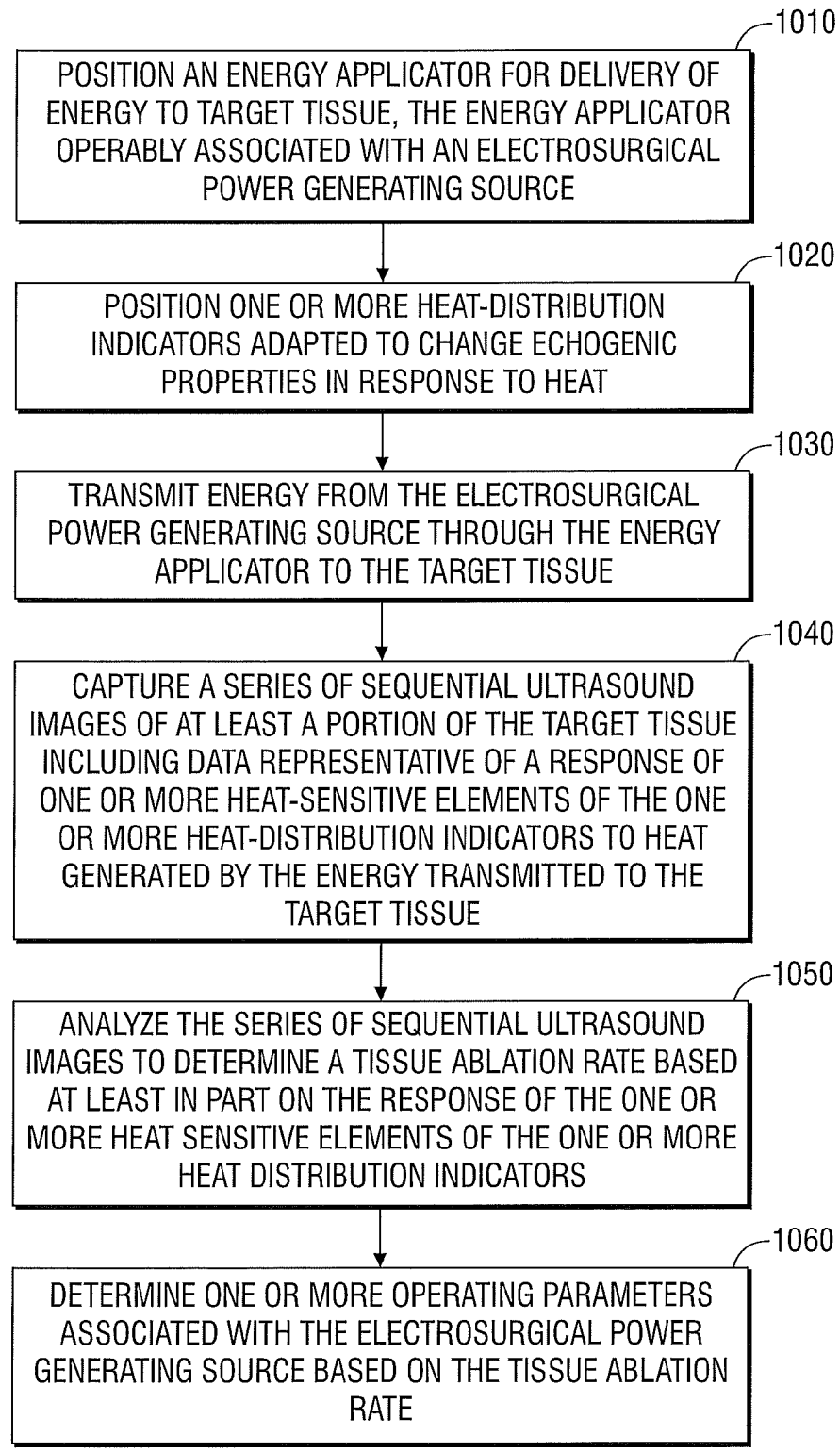
FIG. 10 is a flowchart illustrating a method of directing energy to tissue in accordance with another embodiment of the present disclosure.

FIG. 10 is a flowchart illustrating a method of directing energy to tissue according to an embodiment of the present disclosure. In step 1010, an energy applicator 50 is positioned for delivery of energy to target tissue "T". The energy applicator 50 is operably associated with an electrosurgical power generating source 516.

In step 1020, one or more heat-distribution indicators 300 are positioned. The one or more heat-distribution indicators 300 each include one or more heat-sensitive elements $330_1$-$330_n$ adapted to change echogenic properties in response to heat. In some embodiments, the one or more heat-distribution indicators 300 are positioned relative to the energy applicator 50 and/or the target tissue "T". In some embodiments, one or more heat-sensitive elements $331_1$-$331_n$ of a first portion "P1", a second portion "P2" and/or a third portion "P3" of an echogenic indicator region "R2" may increase in volume and/or decrease in density (or decrease in volume and/or increase in density) when heated to a predetermined temperature or temperature range.

In step 1030, energy from the electrosurgical power generating source 516 is transmitted through the energy applicator 50 to the target tissue "T".

In step 1040, a data set including a series of sequential ultrasound images 800, 810 of at least a portion of the target tissue "T" is captured and includes data representative of a response of one or more heat-sensitive elements $330_1$-$330_n$ of the one or more heat-distribution indicators 300 to heat generated by the energy transmitted to the target tissue "T" by the energy applicator 50. Capturing a series of sequential ultrasound images, in step 1040, may include acquiring one or more ultrasound images using a real-time ultrasonic scanner. In some embodiments, capturing a series of sequential ultrasound images, in step 1040, may additionally, or alternatively, include acquiring one or more ultrasound images from a repository, databank, database, cache, storage unit and/or the like.

In some embodiments, the data set may include DICOM (acronym for Digital Imaging and Communications in Medicine) format images of any part of the body or a full-body scan. However, it will be appreciated that the data set may include image and/or patient data in any standard format, such as without limitation DICOS (Digital Imaging and Communication in Security) format, DICONDE (Digital Imaging and Communication in Nondestructive Evaluation) format, or other format which may include a file format definition and a network communications protocol. The image data may include inter-operatively acquired images and/or pre-operatively acquired images. A subset of the image data may be selectively identified for processing in accordance with any of a variety of methods of image analysis.

In step 1050, the series of sequential ultrasound images 800, 810 is analyzed to determine a tissue ablation rate based at least in part on the response of the one or more heat-sensitive elements $330_1$-$330_n$ of the one or more heat-distribution indicators 330. The tissue ablation rate may be determined by a processor unit 526, e.g., adapted to determine the location of margins of ablated tissue in image data, using image processing of images including data representative of one or more heat-sensitive elements, one or more echogenic indicator regions, or portions thereof (e.g., first portion "P1", second portion "P2" and/or third portion "P3" of echogenic indicator region "R2" shown in FIG. 3C). The determination of a tissue ablation rate may involve any suitable computer-implemented image segmentation method.

In step 1060, one or more operating parameters associated with the electrosurgical power generating source 516 are determined based on the tissue ablation rate. Some examples of operating parameters associated with an electrosurgical power generating source 516 that may be determined include temperature, impedance, power, current, voltage, mode of operation, and duration of application of electromagnetic energy.

Figure 11:
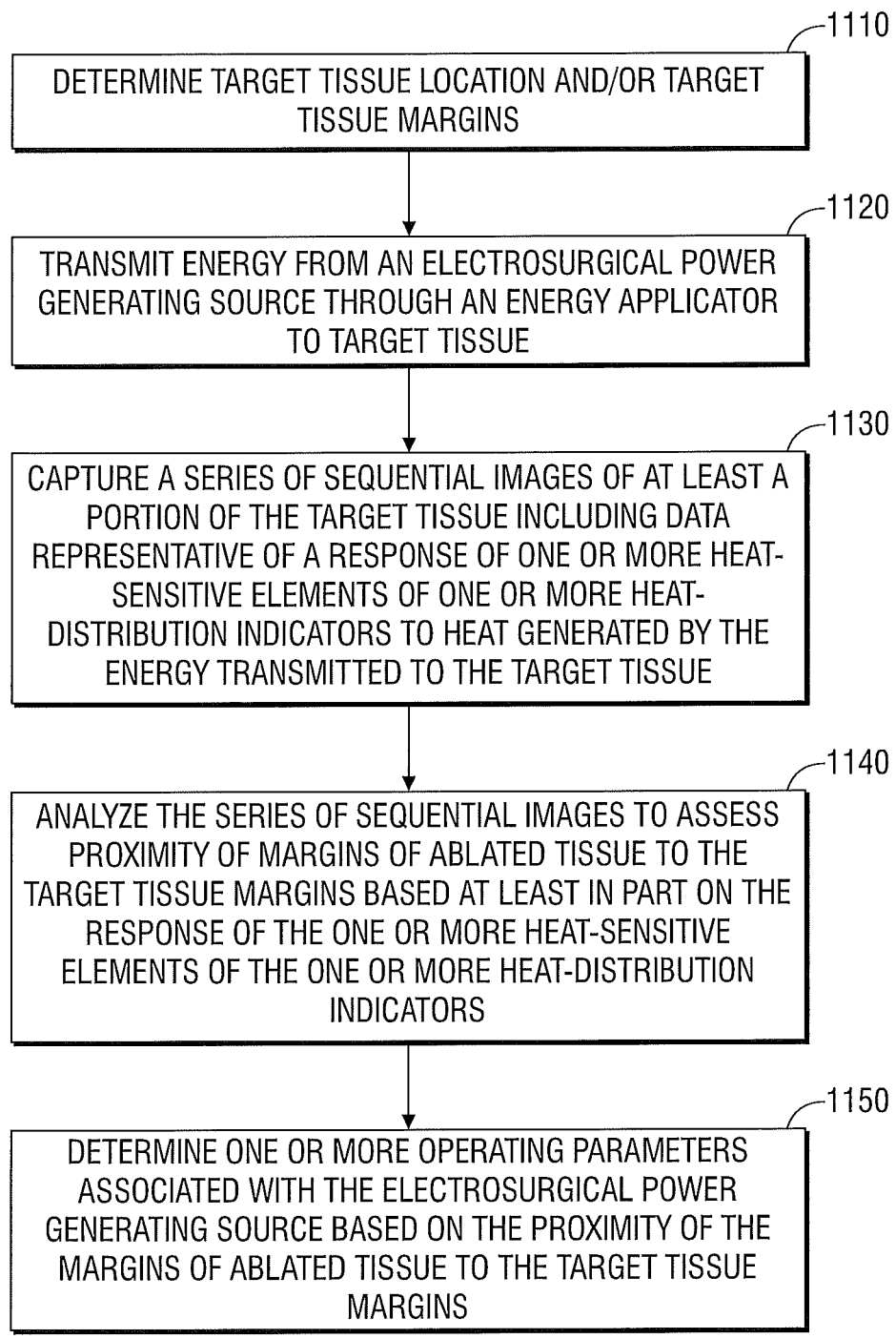
FIG. 11 is a flowchart illustrating a method of directing energy to tissue in accordance with yet another embodiment of the present disclosure.

FIG. 11 is a flowchart illustrating a method of directing energy to tissue according to an embodiment of the present disclosure. In step 1110, target tissue "T" location and/or target tissue "T" margins are determined.

In step 1120, energy from an electrosurgical power generating source 516 is transmitted through an energy applicator 50 to the target tissue "T".

In step 1130, a series of sequential images 800, 810 of at least a portion of the target tissue "T" is captured and includes data representative of a response of one or more heat-sensitive elements $330_1$-$330_n$ of the one or more heat-distribution indicators 300 to heat generated by the energy transmitted to the target tissue "T" by the energy applicator 50.

In step 1140, the series of sequential images 800, 810 is analyzed to assess proximity of margins of ablated tissue to the target tissue "T" margins based at least in part on the response of the one or more heat sensitive elements $330_1$-$330_n$ of the one or more heat-distribution indicators 300.

In step 1150, one or more operating parameters associated with the electrosurgical power generating source 516 are determined based on the proximity of margins of ablated tissue to the target tissue "T" margins.

In some embodiments, safety procedures and/or controls, e.g., control that reduces power level and/or shuts off the power delivery to the energy applicator, may be triggered based on the tissue ablation rate and/or assessment of the ablation margins. In some embodiments, a processor unit 526 configured to generate one or more electrical signals for controlling one or more operating parameters associated with an electrosurgical power generating source 516 may be adapted to reduce power level and/or shut off the power delivery based on the tissue ablation rate and/or the proximity of the margins of ablated tissue to the target tissue margins.

Figure 12:
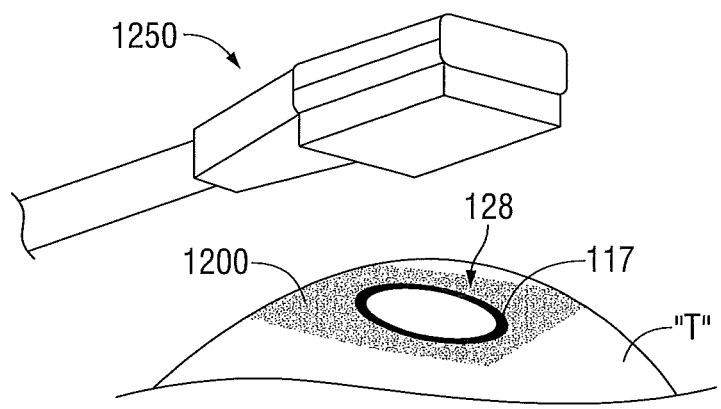
FIG. 12 is a perspective view of a direct-contact, surface-delivery device positioned above tissue, such as after delivery of energy thereto, shown with a diagrammatically-illustrated thermochromic dye applied to a tissue treatment area, according to an embodiment of the present disclosure.
Figure 13:
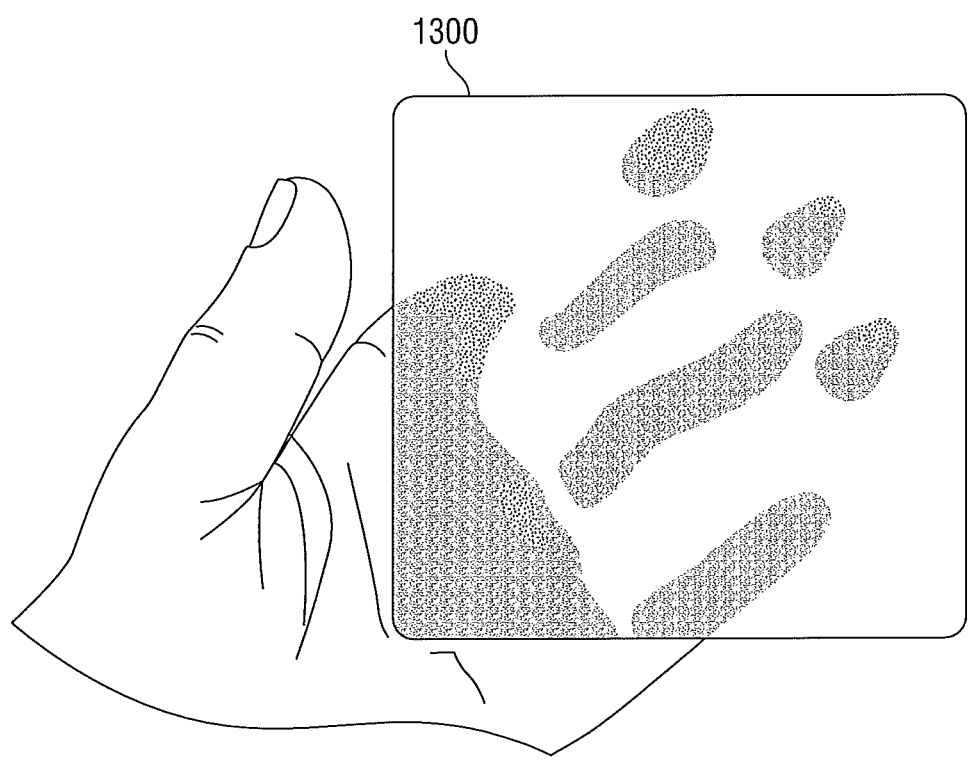
FIG. 13 is a schematic diagram of a film material including thermochromic dye according to an embodiment of the present disclosure.

In FIG. 12 a direct-contact, surface-delivery device 1250 is shown positioned above tissue "T" after the removal of the energy delivery device 1250 from a treatment surface area 128 of the tissue "T", subsequent to the delivery of energy thereto, wherein the treatment surface area 128 includes a thermochromic material 1100 applied thereto, such as prior to the ablation or other heat treatment procedure. In some embodiments, the thermochromic material 1100 may be a thermochromic dye (or a mixture of thermochromic dyes), e.g., applied as a spray or otherwise deposited on the treatment surface area 128. In some embodiments, the thermochromic material 1200 may additionally, or alternatively, be applied as a film. FIG. 13 shows an illustrative example of a film material 1300 including thermochromic pigments. The shape and size of the film material 1300 may be varied from the configuration depicted in FIG. 13.

In various embodiments, the thermochromic material 1200 is an irreversible thermochromic material, and may be used to indicate the margins of ablated tissue (e.g., ring-like region 117 shown in FIG. 12) and/or the progression of the ablation or other heat treatment procedure. The thermochromic material 1200 may be any suitable reversible or irreversible thermochromic material capable of changing color in response to temperature stimuli. In some embodiments, the thermochromic material 1200 may be a mixture of thermochromic dyes having different critical temperature limits. As it is used in this description, "critical temperature" of a thermochromic dye generally refers to the temperature at which the color starts changing in response to the temperature stimuli.

Figure 14:
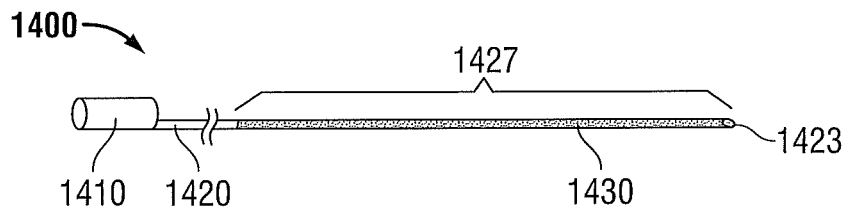
FIG. 14 is a schematic diagram of a thermal zone indicator including a shaft having a thermo-sensitive material extending along a portion of the length thereof according to an embodiment of the present disclosure.

FIG. 14 shows a thermal zone indicator 1400 including a handle member 1410 disposed on a proximal end thereof configured for operable engagement by a user and a shaft 1420 extending distally from the handle member 1410. The shaft 1420 includes a thermo-sensitive material 1430, e.g., an irreversible thermochromic dye, extending along at least a portion of the length thereof. In some embodiments, as shown in FIG. 14, the thermo-sensitive material 1430 is disposed over a region 1427 extending proximally from the distal tip 1423 of the shaft 1420.

Figure 15:
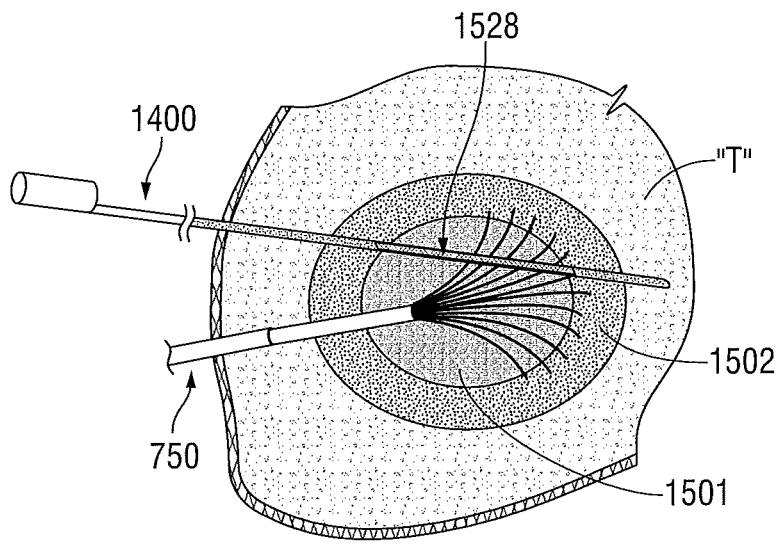
FIG. 15 is a diagrammatic representation of a tissue region, including normal tissue to a region of thermal damage, shown with the thermal zone indicator of FIG. 14 and the energy delivery device of FIG. 7, according to an embodiment of the present disclosure.

FIG. 15 is a diagrammatic representation of a region tissue of "T" shown with the thermal zone indicator 1400 of FIG. 14 and the energy delivery device 750 of FIG. 7. Although, in the illustrative example shown in FIG. 15, the tissue "T" includes first and second zones of thermal damage 1501 and 1502, respectively, it is to be understood that any number of zones of thermal damage may result from the ablation or other heat-treatment procedure.

Figure 16:
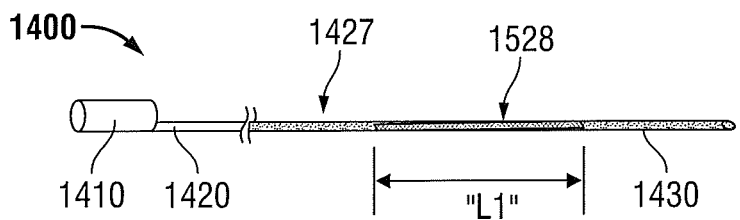
FIG. 16 is a schematic diagram of the thermal zone indicator of FIG. 15, shown exhibiting a region of color change, such as responsive to thermal ablation, according to an embodiment of the present disclosure.

As shown in FIGS. 15 and 16, in response to ablation or other heat-treatment procedure, a portion 1528 of the shaft 1420 having length "L1" (FIG. 16) exhibits change in color, as compared to other portions of the region 1427 adjacent thereto. In alternative embodiments not shown, one or more portions of the thermal zone indicator 1400, e.g., portions disposed with the second zone 1502, may additionally, or alternatively, exhibit change in color, e.g., depending on the material properties of the thermo-sensitive material 1430 and/or the change in temperature by a certain amount in the second zone 1502.

The above-described heat-distribution indicators, thermal zone indicators, electrosurgical devices and systems, and methods of directing energy to target tissue may be suitable for various open and endoscopic surgical procedures.

During a procedure, such as an ablation or other heat treatment procedure, heat may not be uniformly distributed, such as at interfaces having different tissue properties. In some cases, the accurate monitoring of the ablation or other heat treatment procedure may require multi-point measurements of temperature distribution. The above-described heat-distribution indicators and/or thermal zone indicators may be inserted into or placed adjacent to tissue in a variety of configurations, e.g., to allow visual assessment of ablation margins, and/or to allow the surgeon to determine the rate of ablation and/or when the procedure has been completed, and/or to trigger safety procedures and/or controls, e.g., control that reduces power level and/or shuts off the power delivery to the energy applicator.

In the above-described embodiments, one or more operating parameters of an electrosurgical power generating source may be adjusted and/or controlled based on the heat-distribution information provided by the presently-disclosed heat-distribution indicators, e.g., to maintain a proper ablation rate, or to determine when tissue has been completely desiccated and/or the procedure has been completed.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of directing energy to tissue, comprising:
    determining target tissue location and target tissue margins;
    positioning an energy applicator for delivery of energy to target tissue;
    positioning at least one heat-distribution indicator including at least one heat-sensitive element formed of a material having an echogenic property and adapted to phase transition at a predetermined temperature and in response thereto change the echogenic property;
    transmitting energy from an electrosurgical power generating source through the energy applicator to the target tissue;
    acquiring at least one ultrasound image including data representative of a change in the echogenic property of the at least one heat sensitive element of the at least one heat-distribution indicator in response to heat generated by the energy transmitted to the target tissue; and
    determining at least one operating parameter associated with the electrosurgical power generating source based on a tissue ablation rate determined based at least in part on the response of the at least one heat sensitive element of the at least one heat-distribution indicator.

2. The method of directing energy to tissue of claim 1, wherein acquiring the at least one ultrasound image includes:
    acquiring at least one ultrasound image using a real-time ultrasonic scanner; and
    acquiring at least one ultrasound image from a library.

3. The method of directing energy to tissue of claim 1, wherein the energy applicator is mechanically-coupled to the at least one heat-distribution indicator.

4. The method of directing energy to tissue of claim 1, wherein the at least one operating parameter associated with the electrosurgical power generating source is selected from the group consisting of temperature, impedance, power, current, voltage, mode of operation, and duration of application of electromagnetic energy.

5. The method of directing energy to tissue of claim 1, wherein determining the at least one operating parameter associated with the electrosurgical power generating source includes:
    determining a tissue ablation rate based at least in part on the response of the at least one heat sensitive element of the at least one heat-distribution indicator; and
    determining the at least one operating parameter associated with the electrosurgical power generating source based at least in part on the tissue ablation rate.

6. A method of directing energy to tissue, comprising:
    positioning an energy applicator for delivery of energy to target tissue, the energy applicator operably associated with an electrosurgical power generating source;
    positioning at least one heat-distribution indicator including at least one heat-sensitive element formed of a material having an echogenic property and adapted to phase transition at a predetermined temperature and change the echogenic property;
    transmitting energy from the electrosurgical power generating source through the energy applicator to the target tissue;
    capturing a series of sequential ultrasound images of at least a portion of the target tissue including data representative of a change in the echogenic property of the at least one heat-sensitive element of the at least one heat-distribution indicator in response to heat generated by the energy transmitted to the target tissue;
    analyzing the series of sequential ultrasound images to determine a tissue ablation rate based at least in part on the response of the at least one heat-sensitive element of the at least one heat-distribution indicator; and
    determining at least one operating parameter associated with the electrosurgical power generating source based on the tissue ablation rate.

7. The method of directing energy to tissue of claim 6, wherein capturing a series of sequential ultrasound images includes acquiring at least one ultrasound image using a real-time ultrasonic scanner.

8. The method of directing energy to tissue of claim 6, wherein capturing a series of sequential ultrasound images further includes acquiring at least one ultrasound image from a library.

9. The method of directing energy to tissue of claim 6, wherein the at least one heat-distribution indicator is positioned relative to at least one of the energy applicator and the target tissue.

10. The method of directing energy to tissue of claim 7, wherein at least one of the at least one heat-distribution indicators is mechanically-coupled to the energy applicator.

11. The method of directing energy to tissue of claim 6, wherein the at least one operating parameter associated with the electrosurgical power generating source is selected from the group consisting of temperature, impedance, power, current, voltage, mode of operation, and duration of application of electromagnetic energy.

12. A method of directing energy to tissue, comprising:
determining target tissue location and target tissue margins;
transmitting energy from an electrosurgical power generating source through an energy applicator to target tissue;
heating at least one heat-sensitive element of at least one heat-distribution indicator to a predetermined temperature, thereby changing at least one of a volume or a density of the at least one heat-sensitive element, the change in the at least one of the volume or the density of the at least one heat-sensitive element effecting a change of an echogenic property of the at least one heat-sensitive element;
capturing a series of sequential images of at least a portion of the target tissue including data representative of the change in the echogenic property of the at least one heat-sensitive element of the at least one heat-distribution indicator; and
analyzing the series of sequential images to assess proximity of margins of ablated tissue to the target tissue margins based at least in part on the change in the echogenic property of the at least one heat-sensitive element of the at least one heat-distribution indicator.

13. The method of directing energy to tissue of claim 12, wherein the series of sequential images is a series of sequential ultrasound images.

14. The method of directing energy to tissue of claim 12, further comprising determining at least one operating parameter associated with the electrosurgical power generating source based on the proximity of the margins of ablated tissue to the target tissue margins.

15. The method of directing energy to tissue of claim 14, wherein the at least one operating parameter associated with the electrosurgical power generating source is selected from the group consisting of temperature, impedance, power, current, voltage, mode of operation, and duration of application of electromagnetic energy.

* * * * *